United States Patent [19]

Dolak

[11] Patent Number: 4,585,773
[45] Date of Patent: Apr. 29, 1986

[54] ISOINDOLINYL-ALKYL-PIPERAZINES

[75] Inventor: Terence M. Dolak, Evansville, Ind.

[73] Assignee: Bristol-Myers Company, New York, N.Y.

[21] Appl. No.: 629,649

[22] Filed: Jul. 11, 1984

[51] Int. Cl.$^4$ ............... C07D 403/06; A61K 31/495
[52] U.S. Cl. .................................. 514/253; 544/360; 544/373; 544/364
[58] Field of Search ............... 544/360, 373; 424/250

[56] References Cited

U.S. PATENT DOCUMENTS 3,198,798  8/1965  Zinitz et al. ..................... 544/373
3,579,524  5/1971  Van Dyke ......................... 544/373

FOREIGN PATENT DOCUMENTS 0026749  4/1981  European Pat. Off. ............ 546/200
942866  11/1963  United Kingdom ............... 544/373

OTHER PUBLICATIONS

Topliss, J. Med. Chem., vol. 15, 1006–10010, (1972).
Cornish et al., "The Diuretic Activity of Clorexolone and Some Related Phthalimides and 1-Oxoisoindolines", J. Pharm. Pharmacol., 18, 65–80 (1966).
Himori et al., "Antihypertensive Effects of a Combination of a Diuretic and a β-Adrenoceptor Blocking Agent in Conscious Renal Hypertensive Dogs" (Chem. Abs. 90:97589t).
Suzuki et al., "Pharmacological Studies of Diuretics. V. Single and Combination Effects of Diuretic Agents in the Normal or Spontaneously Hypertensive Rats", (Chem. Abs. 81:58265d).

Primary Examiner—George F. Lesmes
Assistant Examiner—S. A. Gibson
Attorney, Agent, or Firm—Robert H. Uloth; Richard P. Ryan

[57] ABSTRACT

The invention is generally concerned with isoindolinyl-alkylpiperazine compounds generally characterized by the formula

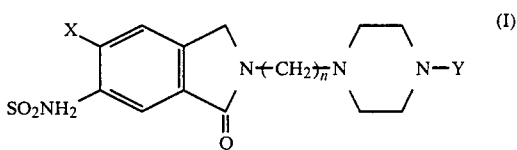

wherein X is halogen or trifluoromethyl; n is an integer ranging from 2 to 5; Y is

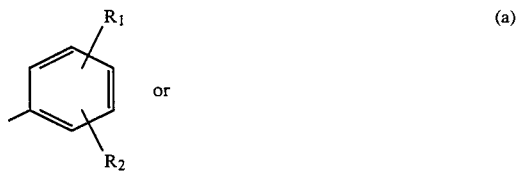

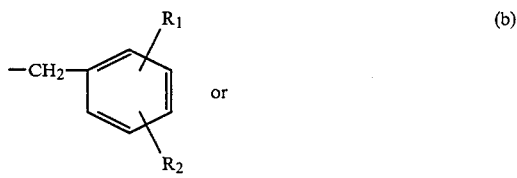

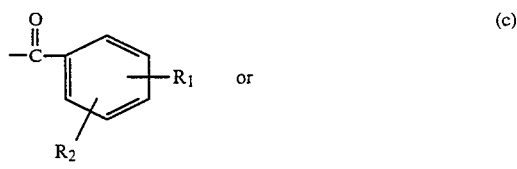

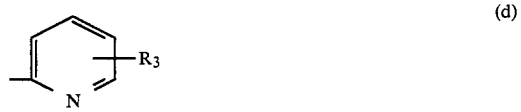

in which $R_1$ is hydrogen, halogen, lower alkyl, lower alkoxy, trifluoromethyl, cyano; $R_2$ is hydrogen, halogen, lower alkyl, lower alkoxy; and $R_3$ is hydrogen, cyano. These compounds are useful as diuretic and/or antihypertensive agents.

23 Claims, No Drawings

ISOINDOLINYL-ALKYL-PIPERAZINES

TECHNICAL FIELD

This invention relates to novel isoindolinyl-alkylpiperazines and to pharmaceutically acceptable salts thereof. Other aspects of the invention concern pharmaceutical compositions containing an instant compound as active ingredient and methods of treatment where there is an indicated need for a diuretic agent and/or an antihypertensive agent.

BACKGROUND OF THE INVENTION

Zenitz et al. U.S. Pat. No. 3,198,798 and Van Dyke U.S. Pat. No. 3,579,524 and British Pat. No. 942,866 disclose 3-oxoisoindole compounds with piperazinylalkylene or substituted piperazinylalkylene moiety on the isoindole N-substiuent. Zenitz et al. discloses antihypertensive utility as well as utility for treating disturbances of the gastrointestinal tract. Van Dyke discloses antihypertensive utility. The British patent discloses that its compounds have anaesthetic, spasmolytic and pectoral properties.

It can be of advantage in the treatment of some disorders to utilize a single drug having both antihypertensive activity and diuretic (especially natriuretic) activity. Usually, the opposite is the case. For example, prazosin, a very active antihypertensive agent has antidiuretic activity.

Thus, there is active research for novel antihypertensive and/or diuretic agents.

For instance, a compound reported in the literature as having diuretic and hypertensive activity is chlorexolone which has the structural formula

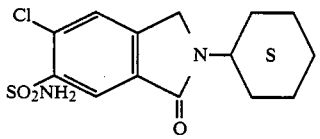

In this regard, see Cornish, et al., J. Pharm. Pharmacol., 18, 65–80 (1966) and Himori, et al., Jpn. J. Pharmacol., 1978, 28(6), 811–818 (Chem. Abs. 90: 97589t) and Suzuki, et al., Nippon Yakurigaku Zasshi, 1972, 63(3), 276–289 (Chem. Abs. 81: 58265d). Cornish, et al. disclose the preparation of phthalimides and 1-oxoisoindolines related to the diuretic chlorexolone. Himori, et al. studied the antihypertensive effect of a combination of chlorexolone and the β-adrenergic blocking agent alprenolol in conscious renal hypertensive dogs and found a significant decrease in blood pressure after the second day of treatment. Suzuki, et al. reported that the hypotensive diuretics, hydroflumethiazide, triamterene, chlorexolone, etc. have favorable effects in the spontaneously hypertensive rat.

Thus, while particular compounds with 6-chloro-5-sulfamoyl isoindolinyl moiety have been known or reputed to have diuretic and antihypertensive activity and while particular isoindolinyl-alkyl-piperazines are disclosed as having antihypertensive activity, 6-chloro-5-sulfamoyl isoindolinyl-alkyl-piperazines have heretofore been unknown.

As used herein the term diuretic means increased total urine flow and/or increased sodium elimination.

SUMMARY OF THE INVENTION

It has now been discovered that 6-halo or trifluoromethyl-2,3-dihydro-3-oxo-5-sulfamoylisoindole compounds bearing particular substituted alkylpiperazine moiety as the isoindole N-substituent have diuretic and/or antihypertensive activity. Preferred compounds herein such as 6-chloro-2,3-dihydro-2-[3-[4-(2-methoxyphenyl)-1-piperazinyl]propyl]-3-oxo-1H-isoindole-5-sulfonamide exhibit both diuretic and antihypertensive properties. Some compounds herein also exhibit in vitro α-binding and in vivo α-block activity.

The compounds of the present invention are those having the structural Formula I

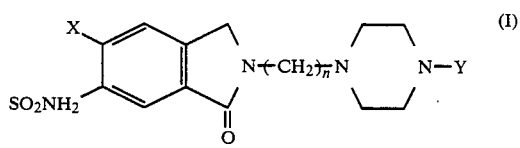

wherein
x is halogen or trifluoromethyl
n is an integer ranging from 2 to 5
y is

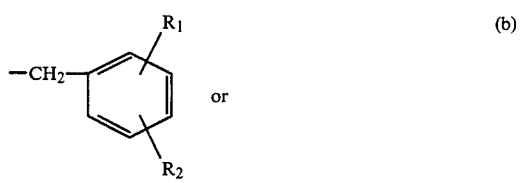

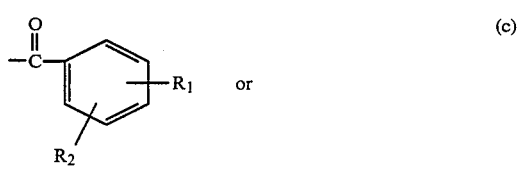

in which
R$_1$ is hydrogen, halogen, lower alkyl, lower alkoxy, trifluoromethyl, cyano,
R$_2$ is hydrogen, halogen, lower alkyl, lower alkoxy,
R$_3$ is hydrogen, cyano, or pharmaceutically acceptable salts thereof.

Preferred compounds are those with the above structural formula wherein X is halogen, very preferably chlorine, n ranges from 2–4, Y is substituted phenyl, i.e. (a), R$_1$ is hydrogen or halogen, very preferably hydrogen, and R$_2$ is hydrogen, lower alkyl or lower alkoxy, very preferably methoxy.

It is to be understood that by employment of the term "lower alkyl" and "lower alkoxy" herein, it is meant that the carbon chains of each group include both straight and branched carbon radicals containing up to 6 carbon atoms, preferably not more than 4 carbon atoms. Exemplary of carbon chain radicals are methyl, ethyl, isopropyl, 1-butyl, 1-methylpropyl, 2-methylpropyl, tert.-butyl, hexyl and the like. Further the term "halogen" used herein connotes all members of that group but preferably chlorine, bromine and fluorine.

The pharmaceutically acceptable salts of the invention are those in which the anion does not contribute significantly to toxicity or pharmacological activity of the salt, and therefore are considered pharmacological equivalents of Formula I bases; these are typically acid addition salts.

For purposes of salt formation of the substances of Formula I, there may be mentioned pharmaceutically acceptable acids such as hydrochloric and other hydrohalic acids, sulphuric, phosphoric, nitric, aliphatic, alicyclic, aromatic or heterocyclic carboxylic acids or sulphonic acids, such as formic, acetic, propionic, succinic, glycollic, lactic, malic, tartaric, citric, ascorbic, maleic, hydroxymaleic or pyruvic, fumaric, benzoic, p-aminebenzoic, anthranilic, p-hydroxy-benzoic, salicyclic, or p-aminosalicyclic, methanesulphonic, ethanesulphonic, hydroxyethanesulphonic, ethylenesulphonic; halogenobenzenesulphonic acid, toluenesulphonic acid, naphthalenesulphonic acid or sulphanilic acid.

Conventional methods are used to prepare the salts. Thus, admixture of a Formula I base with the selected acid in an inert solvent such as water, ethyl acetate, methanol, dimethylformamide and the like with salt isolation by conventional concentration or crystallization techniques are employed.

The compounds herein are readily prepared by the following sequence of steps:

Step 1:

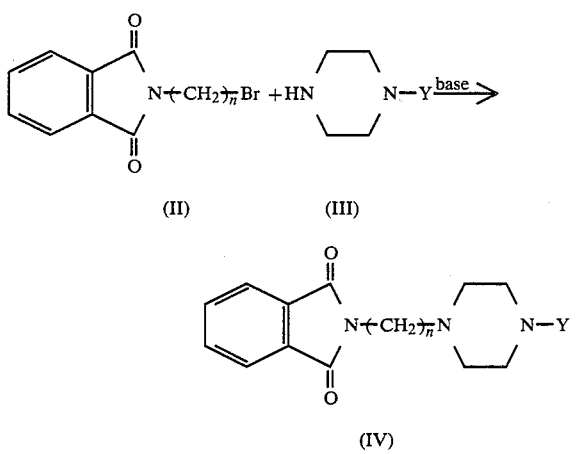

(II)    (III)

(IV)

wherein n and Y are as defined for Formula I.
Step 2:

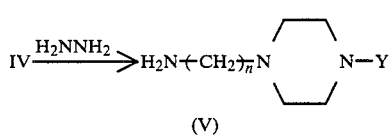

(V)

Step 3:

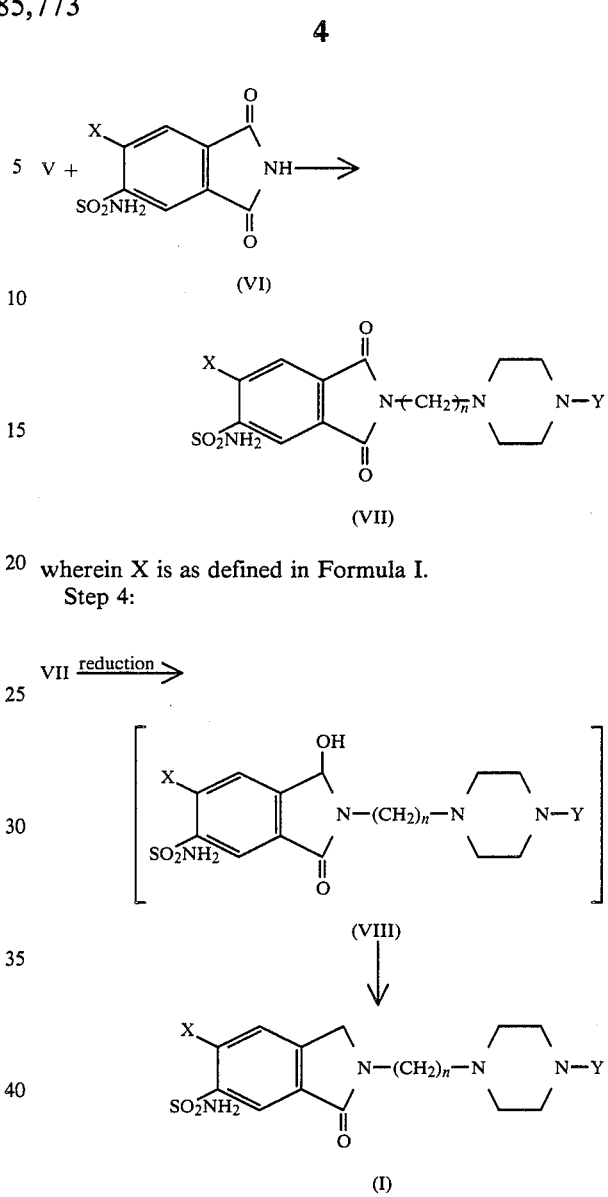

wherein X is as defined in Formula I.
Step 4:

Step 1 is a condensation reaction carried out in the presence of a base which reacts with the HBr which comes off. The reaction is typically carried out, for example, at elevated temperatures of from about 50°-200° C. Solvents which are useful are those typically utilized in reactions between organic halides and amines. The solvent is preferably acetonitrile and can also be, for example, n-pentanol or dimethylformamide. The base is preferably an alkali metal carbonate, e.g. sodium or potassium carbonate, or an organic tertiary amine such as N,N-diisopropylethylamine. Other useful bases include, for example, bicarbonates such as sodium or potassium bicarbonate or alkali metal hydroxides. The reaction may be carried out in the presence of a catalyst such as potassium iodide.

Step 2 is a hydrazine hydrolysis of the phthalimide group and is readily carried out by refluxing the reaction mixture, e.g. in ethanol.

Step 3 is a condensation reaction carried out, for example by refluxing the reaction mixture in n-pentanol and removing the ammonia which is generated.

Step 4 is a reduction reaction wherein the 1,3-dioxoisoindole compounds of Formula VII are reduced to remove the oxo at the 1-position. The reduction is carried out with zinc and acetic acid or tin and concentrated hydrochloric acid at elevated temperatures generally ranging from 60°–150° C. for periods of about 6–48 hours in a reaction inert organic solvent. In the case of zinc-acetic acid, temperatures of 100°–150° C. are preferred and the reduction is conveniently carried out in acetic acid at reflux temperature. Further, reduction with zinc-acetic acid is particularly preferred in that the compounds of Formula I are readily purified by conventional techniques such as basification, extraction and trituration of the extract or precipitation of acid addition salts from crude extracts. In the case of the tin/concentrated hydrochloric acid reduction, preferably carried out at 60°–100° C. in methanol, the Formula I products are more difficult to purify, in some instances, in that they form relatively stable complexes with tin salts. Treatment of the tin complexed Formula I products with hydrogen sulfide under acidic conditions or tetramethylethylenediamine in an inert solvent such as methanol removes the tin as the insoluble sulfide or tetramethylethylenediamine complex, respectively, to provide pure products with respect to elemental analysis but with traces of tin as demonstrated by flame spectrophotometry.

The compounds of Formula VIII are formed during the reduction of the 1,3-dioxoisoindole Formula VII compounds and are considered part of the present invention as valuable intermediates. The Formula VIII compounds can be preferentially obtained and isolated by reducing the Formula VII compounds with excess zinc in acetic acid below 100° C., preferably at or near room temperature.

The foregoing Step 4 reduction is part of the unitary process of the present invention for preparing the compounds characterized by Formula I

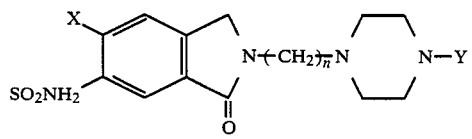

wherein
X is halogen or trifluoromethyl,
n is an integer ranging from 2 to 5,
Y is

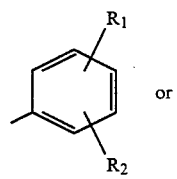 (a) or

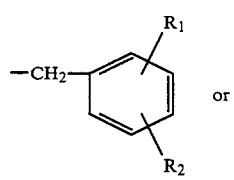 (b) or

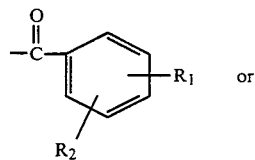 (c) or

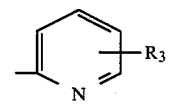 (d)

in which
$R_1$ is hydrogen, halogen, lower alkyl, lower alkoxy, trifluoromethyl, cyano,
$R_2$ is hydrogen, halogen, lower alkyl, lower alkoxy,
$R_3$ is hydrogen, cyano, comprising:

(a) reducing a 1,3-dioxoisoindole compound of Formula VII or a 1-hydroxy-3-oxoisoindole compound of Formula VIII

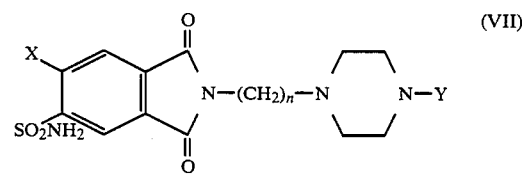 (VII)

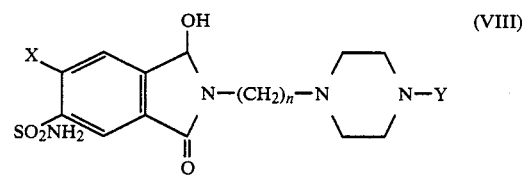 (VIII)

wherein X, n and Y are as defined above; or (b) reacting a 4-aminopiperazine compound of Formula V

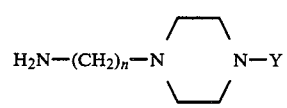 (V)

wherein n and Y are as defined above with a sulfamoyl compound of Formula IX in an inert solvent

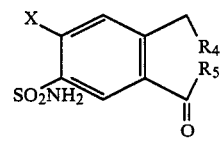 (IX)

wherein X is as defined above, $R_5$ is amino, halogen, lower alkoxy; and $R_4$ is halogen or taken as the radical $R_4CH_2$— is carbamoyl or formyl; and $R_5$ and $R_4$ taken together is oxygen;

(c) reacting a piperazinyl compound of Formula X

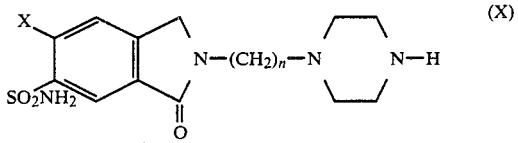 (X)

wherein n and X are as defined above with a compound of Formula XI

Z-Y          (XI)

wherein Y is as defined above and Z is a reactive leaving group.

It is to be understood that the sulfamoyl intermediates of Formula IX particularly comprehend such compounds as:

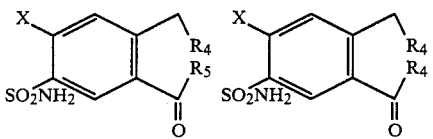

IXa    IXb

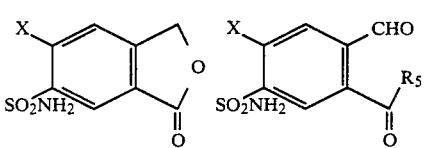

IXc    IXd

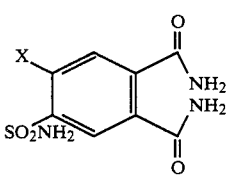

IXe and preferably those wherein X is halogen or trifluoromethyl, $R_5$ is lower alkoxy, preferably methoxy and $R_4$ is halogen.

Known methods are employed in preparation of the Formula IX and X intermediates as illustrated by European Patent Application No. 26,749.

Regarding the reaction of a piperazinyl compound of Formula X with a compound of Formula XI, an inert organic solvent such as n-pentanol or dimethylformamide is employed at elevated temperature of from about 50°-200° in the presence of a basic condensation agent, preferably an alkali metal hydroxide, carbonate or bicarbonate, for example sodium carbonate, potassium carbonate, sodium bicarbonate or potassium bicarbonate, or an organic tertiary nitrogen amine bases; such as triethylamine or pyridine. The Formula X intermediate is obtained from a compound of Formula I wherein the Y-radical is benzyl by catalytic debenzylation. Formula XI compounds are commercially available or prepared as described herein. The term "reactive leaving group" as used with respect to "Z" in Formula XI refers to a reactive esterified hydroxy group such as that obtained when esterified by strong inorganic or organic acids such as hydrochloric, hydrobromic, hydroiodic acid, sulfuric acid, or an organic sulfonic acid, for example, benzenesulfonic, p-bromobenzenesulfonic, or p-toluenesulfonic acid. Particularly preferred leaving groups are chlorine or bromine.

The compounds of Formula I have antihypertensive and/or diuretic properties as can be demonstrated by standard pharmacological test models known to correlate with effects in man. With respect to antihypertensive utility, there can be mentioned such conventional models as the spontaneously hypertensive and DOCA-salt hypertensive rat. Typical tests are conducted as follows:

Spontaneously Hypertensive Rat

Male rats weighing 300-400 g, previously conditioned to the procedure, are prewarmed in a heating chamber (30° C.) for 10-20 min. and subsequently restrained in a wire holder at that temperature. Systolic blood pressure and heart rate are measured by the tail-cuff technique using a pneumatic pulse transducer and a biotachometer before, and 2, 4, and 24 hours after oral administration of vehicle (0.25% Methocel in water) or test compounds suspended in vehicle at a dose volume equivalent to 5 ml/kg. Blood pressure and heart rate data are reported as changes from zero-hour measurements with vehicle control groups run periodically to confirm that the vehicle has no effect.

DOCA-salt Hypertensive Rat

Male rats initially weighing 80-100 g, are made hypertensive by surgically implanting two 50 mg pellets of deoxycorticosterone acetate (DOCA) under the skin of the abdomen of each rat and providing 1% saline ad libitum. After three weeks, the 1% saline is replaced with distilled water. One week later, animals are anesthetized with methoxyflurane and a catheter advanced into the aorta via the left common corotid artery to record mean arterial blood pressure (MABP) and heart rate. The heparin-filled catheter is passed beneath the skin and exteriorized behind the head. Two days later, MABP and heart rate are determined before and four hours after oral administration of vehicle (0.25% Methocel in 0.9% saline) or test compound suspended in vehicle at a dose volume equivalent to 5 ml/kg.

With respect to diuretic utility there can be mentioned the conscious rat diuretic screen of Lipschitz, et al. (J. Pharmacol. Exp. Therap. 79, 97–110 (1943)). In this test, dose response assays of diuretic, natruiretic and kaliuretic activity are determined by oral administration of the test substance.

As indicated above, a preferred compound herein having both diuretic and antihypertensive action is 6-chloro-2,3-dihydro-2-[3-[4-(2-methoxyphenyl)-1-piperazinyl]propyl]-3-oxo-1H-isoindole-5-sulfonamide (referred to herein as MJ 15037). It has a dose-dependent natriuretic response in a dose range of 3.0 to 30 mg/kg body weight. As an antihypertensive, MJ 15037 demonstrates activity in the DOCA-hypertensive rat and spontaneously-hypertensive rat. In the latter, MJ 15037 exhibits a dose-dependent decrease in systolic blood pressure following doses at 3.0 to 30 mg/kg body weight with antihypertensive effect seen at about two hours. MJ 15037 also demonstrates activity in binding both $\alpha_1$ and $\alpha_2$ sites.

As stated above, Formula 1 compounds have diuretic and/or antihypertensive properties with those having complimentary diuretic and antihypertensive activity preferred. Thus, another embodiment of the instant invention is directed to a process for treating hypertension comprising systemically administering to a mammal in need of such treatment an antihypertensive effective amount of a compound of Formula I or a pharmaceutically acceptable acid addition salt thereof. Preferred compounds are the Example I, II, III, IV, V, IX, X, XI and XII products of Formula I and most preferably 6-chloro-2,3-dihydro-2-[3-[4-(2-methoxyphenyl)-1-piperazinyl]propyl]-3-oxo-1H-isoindole-5-sulfonamide. By systemic administration, it is intended to include both oral and parenteral routes with oral being preferred. Examples of parenteral administration are intramuscular, intravenous, intraperitoneal, rectal and subcutaneous administration. The dosage will vary with the form of administration and the particular compound chosen. However, from about 0.1 to 50 mg per kg of body weight of a mammal of a compound characterized by Formula I administered in effective single or multiple dosage units is generally satisfactory. In accordance with conventional clinical practice, a Formula I compound is administered at a dosage substantially less than the dose of the compound which is thought to be effective. If the antihypertensive and/or diuretic response is insufficient after a suitable trial, dosage is increased by small increments until the optimum effect is reached.

When administered as an antihypertensive in general clinical practice, the Formula I compound is given orally in a daily dose of from 3 to 300 mg and preferably 7 to 280 mg in a manner similar to prazocin. For parenteral administration, a suitable dose is generally proportionally less and is usually from one-tenth to one-third of the dose suggested for oral administration.

In carrying out the antihypertensive and/or diuretic process, the active ingredient of Formula I and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutically acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspensions, syrups, and elixirs may contain the active ingredients in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectible compositions are formulated as known in the art and may contain appropriate dispersing or wetting agents and suspending agents identical or similar to those mentioned above.

The following examples are illustrative of the invention. All temperatures are degrees centigrade and melting points taken with a Thomas Hoover capillary apparatus are uncorrected.

EXAMPLE I

6-Chloro-2,3-dihydro-2-[3-[4-(2-methoxyphenyl)-1-piperazinyl]propyl]-3-oxo-1H-isoindole-5-sulfonamide

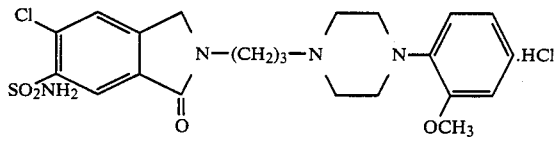

was prepared in the following steps:

Step (a): Preparation of N-[3-[4-(2-methoxyphenyl)-1-piperazinyl]propyl]phthalimide A mixture of 1-(o-methoxyphenyl)piperazine (0.19 mol), N-(3-bromopropyl)phthalimide (0.186 mol) and micropulverized potassium carbonate (0.465 mol) in acetonitrile (375 ml) was heated at reflux for 16 hours. The cooled mixture was evaporated in vacuo and the residue diluted with water (800 ml) and extracted with chloroform (4×350 ml). After drying (MgSO$_4$), the combined extracts were evaporated in vacuo. The residue was dried under high vacuum (<0.05 mm of Hg) at room temperature for 16 hours resulting in 72.0 g of a yellow solid ~100% yield); mp 85°–93° C. Spectral data were consistent with the assigned structure.

Step (b): Preparation of 1-(3-amino-1-propyl)-4-(2-methoxyphenyl)piperazine

A mixture of the compound formed in (a) above (0.184 mol) and hydrazine hydrate (0.184 mol) in ethanol (750 ml) was heated at reflux for 16 hours. The cooled suspension was filtered and the filtrate made basic (pH of 10) with 10% sodium hydroxide solution resulting in a white suspension. Volatiles were removed in vacuo and the residue diluted with water (400 ml). The product was extracted with chloroform (5×400 ml). After drying (MgSO$_4$), the combined extracts were evaporated in vacuo and the resulting orange oil was placed under high vacuum (<0.05 mm of Hg) for 16 hours affording 43.6 g of orange oil (95% yield). Spectral data are consistent with the assigned structure. This material was used without further purification.

Step (c): Preparation of 6-chloro-2-[3-[4-(2-methoxyphenyl)-1-piperazinyl]propyl]-2,3-dihydro-1,3-dioxo-1H-isoindole-5-sulfonamide A mixture of 4-chloro-5-sulfamoyl phthalimide (0.076 mol) and the compound formed in (b) above (0.076 mol) in n-pentanol (375 ml) was heated at reflux for 16 hours. A gas inlet tube was placed just above the solvent surface and dry nitrogen was introduced during reflux to facilitate the removal of generated ammonia. On cooling, a solid precipitated and was collected by filtration. Trituration with diethyl ether gave 22.8 g of a yellow solid (61% yield); mp 121°–137° C. Spectral data are consistent with the assigned structure and also indicated a slight (<2%) n-pentanol impurity. This material was used without further purification.

Further pentanol-ether treatment of a sample provided pale yellow material, 134°–137° C.

Analysis: Calculated for $C_{22}H_{25}ClN_4O_5S \cdot H_2O$: C, 51.71; H, 5.33; N, 10.96; $H_2O$, 3.53. Found: C, 51.71; H, 5.36; N, 10.72; $H_2O$, 3.09.

Step (d): Preparation of Title Product

A mixture of the compound formed in Step (c) above (0.045 mol) and zinc dust (0.25 mol) in glacial acetic acid (500 ml) was stirred at room temperature for 1 hour. The suspension was then heated at reflux for 4 hours. The cooled mixture was filtered to remove excess zinc and zinc salts. The filter cake was washed with acetic acid (50 ml) and the combined filtrates evaporated in vacuo to give an orange oil. Saturated aqueous sodium bicarbonate (250 ml) and ethyl acetate (300 ml) were added to the residue oil. Layers were separated and the aqueous phase extracted with ethyl acetate (5×300 ml). The combined extracts were dried ($MgSO_4$) and evaporated in vacuo. The residue was dissolved in hot ethyl acetate (50 ml) and treated with 8.9N ethanolic hydrogen chloride (10 ml) resulting in the immediate precipitation of a beige solid. The cooled suspension was filtered and the cake pulverized and dried under high vacuum (<0.05 mm of Hg) at 110° C. for 16 hours resulting in 17.8 g (77% yield) of analytically pure 6-chloro-2-[3-[4-(2-methoxyphenyl)-1-piperazinyl]propyl]-3-oxo-1H-isoindole-5-sulfonamide as the hydrochloride salt (denoted MJ 15037-1); mp 158°–170° C. (dec.); a beige solid. The compound has diuretic, antihypertensive and alpha binding utility.

Analysis Calculated for $C_{22}H_{27}ClN_4O_4S \cdot HCl$: C, 51.26; H, 5.48; N, 10.87. Found: C, 51.11; H, 5.61; N, 10.90.

NMR (DMSO-$d_6$): 2.18 (2,m); 3.15 (6,m); 3.53 (6,m); 3.77 (3,s); 4.62 (2,s); 6.94 (4,m); 7.78 (2,bs); 7.95 (1,s); 8.20 (1,s); 11.43 (1,bs).

IR (KBr): 755, 1020, 1170, 1240, 1330, 1450, 1500, 1615, 1675.

The hydrochloride salt of the title product prepared as described above was suspended in isopropanol (12 ml/g) and heated on a steam bath for 0.5 hours, filtered hot and washed with isopropanol. The product was dried in a vacuum oven at 80° C. to afford analytically pure 6-chloro-2,3-dihydro-2-[3-[4-(2-methoxyphenyl)-1-piperazinyl]propyl]-3-oxo-1H-isoindole-5-sulfonamide as the ¾ mole hydrochloride salt (denoted MJ 15037-1A); mp 270°–272° C. (dec.).

Analysis: Calculated for $C_{22}H_{27}ClN_4O_4S \cdot \frac{3}{4}HCl$: C, 52.19; H, 5.52; N, 11.06; Cl, 12.25. Found: C, 52.36; H, 5.66; N, 11.02; Cl, 11.90.

NMR (DMSO-$d_6$): 2.20 (2,m); 3.15 (6,m); 3.50 (6,m); 3.79 (3,s); 4.65 (2,s); 6.95 (4,m); 7.80 (2,bs); 7.96 (1,s); 8.22 (1,s); 11.50 (1,bs).

IR (KBr): 750, 1020, 1170, 1245, 1335, 1450, 1500, 1615, 1685.

A sample of the title product prepared as the hydrochloride salt was triturated with hot isopropanol and subsequently dried under vacuum at about 100° C. for a 72 hour period to provide 6-chloro-2,3-dihydro-2-[3-[4-(2-methoxyphenyl)-1-piperazinyl]propyl]-3-oxo-1H-isoindole-5-sulfonamide monohydrochloride as 2-propanolate solvated material (denoted MJ 15037–1–3), mp 278°–279° (dec.) having the following analytical and NMR data.

Analysis: Calculated for $C_{22}H_{27}ClN_4O_4S \cdot HCl$ $0.2C_3H_8O \cdot 0.15H_2O$: C, 51.20; H, 5.68; N, 10.57; $H_2O$, 0.51. Found: C, 51.52; H, 5.75; N, 10.51; H, 0.77.

NMR (DMSO-$d_6$): 2.17 (2,m); 3.12 (6,m); 3.44 (6,m); 3.76 (3,s); 4.63 (2,s); 6.92 (4,m); 7.75 (2,bs); 7.94 (1,s); 8.20 (1,s).

IR (KBr): 750, 1245, 1165, 1330, 1500, 1615, 1670.

EXAMPLE II

6-Chloro-2-[3-[4-(3-chlorophenyl)-1-piperazinyl]propyl]-2,3-dihydro-3-oxo-1H-isoindole-5-sulfonamide hydrochloride hemihydrate

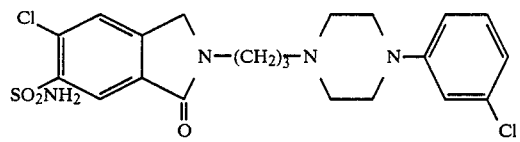

was prepared as the hydrochloride hemihydrate in the following steps:

Step (a): Preparation of N-[3-[4-(3-chlorophenyl)-1-piperazinyl]propyl]phthalimide A mixture of 1-(m-chlorophenyl)piperazine (0.025 mol), N-(3-bromopropyl)phthalimide (0.025 mol), N,N-diisopropylethylamine (0.025 mol) and potassium iodide (0.003 mol) in acetonitrile (20 ml) was heated at reflux for 16 hours. The cooled mixture was evaporated in vacuo. Water (100 ml) was added to the dark residue and the product extracted with chloroform (4×125 ml). The combined extracts were washed with water (100 ml), dried over $MgSO_4$ and evaporated in vacuo affording 10.7 g of an orange oil which solidified on standing. Trituration with absolute ethanol afforded 10.2 g of a white solid (98% yield). Spectral data are consistent with the assigned structure.

Step (b): Preparation of 1-(3-amino-1-propyl)-4-(3-chlorophenyl)piperazine

This preparation was carried out the same as Step (b) of Example 1 except that 0.025 mol of the product of Step (a) herein was used in place of the product of Step (a) of Example 1 and the hydrazine was utilized in an amount providing the same molar ratio of reactants as used in Step (b) of Example 1. Reaction gave 5.1 g of a clear oil (80% yield). Spectral data are consistent with the assigned structure. This material was used without further purification.

Step (c): Preparation of 6-chloro-2-[3-[4-(3-chlorophenyl)-1-piperazinyl]propyl]-2,3-dihydro-1,3-dioxo-1H-isoindole-5-sulfonamide This was carried out by the method and molar ratios of Step (c) of Example I with 0.019 mol of the product of Step (b) herein being utilized in place of the product of Step (b) of Example I. Reaction provided a waxy solid. This material was collected and triturated with acetonitrile giving 5.95 g of a yellow solid (62% yield); mp 192°–195° C. (dec.). Spectral data are consistent with the assigned structure. This material was used without further purification.

Step (d): Preparation of the Title Product

This was carried out by the method and molar ratios of Step (d) of Example I with 0.012 mol of the product of Step (c) herein being utilized in place of the product of Step (c) of Example I. Reaction afforded 5.2 g of a foamy residue. This material was dissolved in hot ethyl acetate (150 ml), treated with 9N ethanolic hydrogen chloride (3.5 ml) and the mixture cooled to room temperature. The filtered solid was triturated with acetonitrile, collected by filtration and dried under vacuum (<0.05 mm of Hg) at 100° C. for 16 hours resulting in 5.0 g (79% yield) of analytically pure 6-chloro-2-[3-[4-(3-chlorophenyl)-1-piperazinyl]propyl]-2,3-dihydro-3-oxo-1H-isoindole-5-sulfonamide hydrochloride as the hemihydrate; mp 140°–175° C. (dec.); a white solid.

Analysis: Calculated for $C_{21}H_{24}Cl_2N_4O_3S \cdot HCl \cdot 0.5 H_2O$: C, 47.69; H, 4.96; N, 10.59; $H_2O$, 1.70. Found: C, 47.99; H, 5.03; N, 10.65; $H_2O$, 1.64.

Spectral data are consistent with the assigned structure.

EXAMPLE III

6-Chloro-2,3-dihydro-2-[2-[4-(2-methoxyphenyl)-1-piperazinyl]ethyl]-3-oxo-1H-isoindole-5-sulfonamide

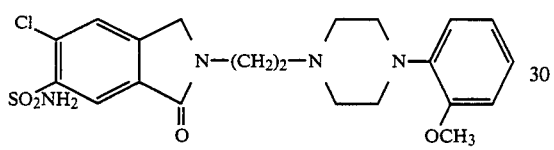

was prepared in the following steps:

Step (a): Preparation of N-[2-[4-(2-methoxyphenyl)-1-piperazinyl]ethyl]phthalimide This was carried out with the method and molar ratios of Step (a) of Example I with 0.026 mol of N-(2-methoxyphenyl)piperazine being utilized and with N-(2-bromoethyl)phthalimide being utilized in place of N-(3-bromopropyl)phthalimide. The reaction afforded 4.25 g of a white solid (45% yield); mp 76°–81° C. Spectral data are consistent with the assigned structure. This material was used without further purification.

Step (b): Preparation of 1-(2-amino-1-ethyl)-4-(2-methoxyphenyl)piperzine

This was carried out by the method and molar ratios of Step (b) of Example I except that the 0.012 mol of the reaction product of Step (a) herein was utilized in place of the reaction product of Step (a) of Example I. Reaction provided 2.12 g of a clear oil (75% yield). Spectral data are consistent with the assigned structure. This material was used without further purification.

Step (c): Preparation of 6-chloro-2-[2-[4-(2-methoxyphenyl)-1-piperazinyl]ethyl-2,3-dihydro-1,3-dioxo-1H-isoindole-5-sulfonamide This was carried out by the method and molar ratios of Step (c) of Example I except that 0.009 mol of the product of Step (b) herein was utilized in place of the product of Step (b) of Example I. Reaction afforded a brown precipitate. Trituration of this material with hexane-dioxane (3:1) gave 3.25 g of a tan precipitate (80% yield); mp 198°–214° C. Spectral data are consistent with the assigned structure. This material was used without further purification.

Step (d): Preparation of Title Product

Reaction was carried out by the method and molar ratios of Step (d) of Example I except that 0.007 mol of the product of Step (c) herein was used in place of the product of Step (c) of Example I. Reaction gave a yellow oil. This material was diluted with ethyl acetate (10 ml) and allowed to crystallize. The pale yellow solid was collected and dried under vacuum (<0.05 mm of Hg) at room temperature for 72 hours resulting in 0.97 g (32% yield) of analytically pure 6-chloro-2,3-dihydro-2-[4-(2-methoxyphenyl)-1-piperazinyl]ethyl]-3-oxo-1H-isoindole-5-sulfonamide; mp 212°–215° C. (dec.); a pale yellow solid.

Analysis: Calculated for $C_{21}H_{25}ClN_4O_4S$: C, 54.25; H, 5.42; N, 12.05. Found: C, 54.25; H, 5.37; N, 11.92.

Spectral data are consistent with the assigned structure.

EXAMPLE IV

6-Chloro-2,3-dihydro-2-[3-[4-(2-methylphenyl)-1-piperazinyl]propyl]-3-oxo-1H-isoindole-5-sulfonamide

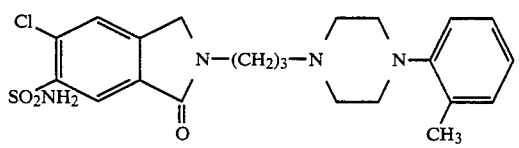

was prepared in the following steps:

Step (a): Preparation of N-[3-[4-(2-methylphenyl)-1-piperazinyl]propyl]phthalimide Reaction was carried out by the method and molar ratios of Step (a) of Example II except that N-(2-methylphenyl)piperazine (0.028 mol) was used in place of the 1-(m-chlorophenyl)piperazine. Reaction gave 11.1 g of an orange oil. Spectral data are consistent with the assigned structure. This material was used without further purification.

The starting material, N-(2-methylphenyl)piperazine, was prepared from the corresponding dihydrochloride salt by adding the salt portionwise to a solution of sodium metal (0.087 mol) in methanol (150 ml) at room temperature. The resulting mixture was stirred at room temperature for 4 hours. Precipitated sodium chloride was removed by filtration. The filtrate was evaporated in vacuo and the residue triturated with acetonitrile (50 ml). The mixture was filtered and the filtrate evaporated in vacuo affording 7.15 g of a yellow oil (~100% yield). Spectral data are consistent with the free base. This material was used without further purification.

Step (b): Preparation of 1-(3-amino-1-propyl)-4-(2-methylphenyl)piperazine

Reaction was carried out by the method and molar ratios of Step (b) of Example I except that the product of Step (a) herein (0.028 mol) was utilized in place of the product of Step (a) of Example I. Reaction afforded 6.5 g of an orange oil (98.5% yield). Spectral data are consistent with the assigned structure. This material was used without further purification.

Step (c): Preparation of 6-chloro-2-[3-[4-(2-methylphenyl)-1-piperazinyl]-propyl]-2,3-dihydro-1,3-dioxo-1H-isoindole-5-sulfonamide Reaction was carried out by the method and molar ratios of Step (c) of Example I except that the product of Step (b) herein (0.02 mol) was utilized in place of the product of Step (b) of Example I. Reaction afforded a yellow solid. This material was triturated with ether affording 4.3 g of a yellow solid (45% yield); mp 133°–145° C. (dec.). Spectral data are consistent with the assigned structure. This material was used without further purification.

Step (d): Preparation of Title Product

Reaction was carried out by the method and molar ratios of Step (d) of Example I except that the product of Step (c) herein (0.009 mol) was utilized in place of the product of Step (c) of Example I. Reaction afforded 3.5 g of a beige waxy solid. This material was triturated with isopropanol (50 ml), the suspension filtered and the the precipitate dried under vacuum (40–50 mm of Hg) at 50° C. for 16 hours resulting in 2.2 g (50% yield) of analytically pure 6-chloro-2,3-dihydro-2-[3-[4-(2-methylphenyl)-1-piperazinyl]propyl]-3-oxo-1H-isoindole-5-sulfonamide; mp 193°–198° C. (dec.), a beige solid.

Analysis: Calculated for $C_{22}H_{27}ClN_4O_3S$: C, 57.07; H, 5.88; N, 12.10. Found: C, 57.30; H, 6.00; N, 11.85.

Spectral data are consistent with the assigned structure.

EXAMPLE V

6-Chloro-2,3-dihydro-3-oxo-2-[3-[4-(phenylmethyl)-1-piperazinyl]propyl]-1H isoindole-5-sulfonamide

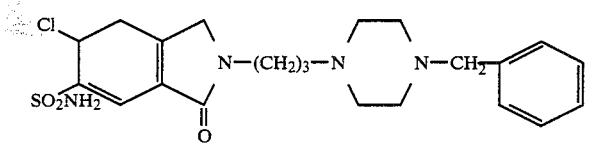

was prepared in the following steps:

Step (a): Preparation of N-[3-[4-(phenylmethyl)-1-piperazinyl]propyl]phthalimide Reaction was carried out by the method and molar ratios of Step (a) of Example II except that 1-benzylpiperazine (0.028 mol) was used in place of the 1-(m-chlorophenylpiperazine). Reaction gave 10.5 g of an orange oil (100% yield). Spectral data are consistent with the assigned structure. This material was used without further purification.

Step (b): Preparation of 1-(3-amino-1-propyl)-4-(phenylmethyl)piperazine

Reaction was carried out by the method and molar ratios of Step (b) of Example I except that the product of Step (a) herein (0.028 mol) was used in place of the product of Step (a) of Example I. Reaction gave 6.1 g of a clear oil (92% yield). Spectral data are consistent with the assigned structure. This material was used without further purification.

Step (c): Preparation of 6-chloro-2-[3-[4-(phenylmethyl)-1-piperazinyl]propyl]-2,3-dihydro-1,3-dioxo-1H isoindole-5-sulfonamide Reaction was carried out by the method and molar ratios of Step (c) of Example I except that the product of Step (b) herein (0.021 mol) was used in place of the product of Step (b) of Example I. Reaction afforded 7.7 g of a yellow solid (77% yield); mp 180°–183° C. Trituration of a portion (1.6 g) of this material with methanol gave 1.3 g of a yellow solid; mp 180°–183° C. (dec.).

Analysis Calculated for $C_{22}H_{25}ClN_4O_4S$: C, 55.40; H, 5.28; N, 11.75. Found: C, 55.73; H, 5.55 and N, 11.48. Spectral data are consistent with the assigned structure.

Step (d): Preparation of Title Product

Reaction was carried out by the method and molar ratios of Step (d) of Example I except that the product of Step (c) herein (0.013 mol) was utilized in place of the product of Step (c) of Example I. Reaction afforded a white solid which was triturated with ethyl acetate-ether (1:1) and the suspension filtered. The precipitate was dried under vacuum (<0.05 mm of Hg) at 80° C. for 16 hours affording 4.3 g (74% yield) of analytically pure 6-chloro-2,3-dihydro-3-oxo-2-[3-[4-(phenylmethyl)-1-piperazinyl]propyl]-1H-isoindole-5-sulfonamide; mp 187°–191° C. (dec.); a white solid.

Analysis: Calculated for $C_{22}H_{27}ClN_4O_3S$: C, 57.07; H, 5.88; N, 12.10. Found: C, 57.16; H, 5.52; N, 12.07.

Spectral data are consistent with the assigned structure.

EXAMPLE VI

6-Chloro-2-[3-[4-(3-cyano-2-pyridinyl)-1-piperazinyl]-propyl]-2,3-dihydro-3-oxo-1H-isoindole-5-sulfonamide

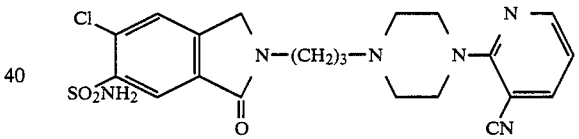

was prepared as the hydrochloride hydrated material in the following steps:

Step (a): Preparation of 1-(3-cyano-2-pyridinyl)piperazine

A mixture of piperazine (0.5 mol) and 2-chloro-3-cyanopyridine (0.1 mol) in absolute ethanol (225 ml) was heated at reflux for 16 hours. The cooled mixture was filtered to remove precipitated piperazine hydrochloride and the filtrate evaporated in vacuo. The residue was diluted with water (200 ml), made basic (pH>10) with 5N sodium hydroxide and extracted with ether (5×300 ml). The combined extracts were dried (MgSO4) and evaporated in vacuo affording 13.6 g of a white solid (72.5% yield); mp 99°–103° C. Spectral data are consistent with the assigned structure. This material was used without further purification.

Step (b): Preparation of N-[3-[4-(3-cyano-2-pyridinyl)-1-piperazinyl]propyl]phthalimide Reaction was carried out by the method and molar ratios of Step (a) of Example II except that the product formed in Step (a) in this Example (0.037 mol) was used in place of the 1-(m-chlorophenyl)piperazine. Reaction gave 14.1 g of an orange oil (~100% yield). Spectral data are consistent with the assigned structure. This material was used without further purification.

Step (c): Preparation of 1-(3-amino-1-propyl)-4-(3-cyano-2-pyridinyl)piperazine

Reaction was carried out by the method and molar ratios of Step (b) of Example I except that the product formed in Step (b) of this Example was used in place of the product of Step (a) of Example I. Reaction afforded 7.6 g of an orange oil (83.5% yield). Spectral data are consistent with the assigned structure. This material was used without further purification.

Step (d): Preparation of 6-chloro-2-[3-[4-(3-cyano-2-pyridinyl)-1-piperazinyl]-propyl]-2,3-dihydro-1,3-dioxo-1H-isoindole-5-sulfonamide Reaction was carried out by the method and molar ratios of Step (c) of Example I except that the product of Step (c) herein (0.021 mol) was used in place of the product of (b) of Example I. Reaction gave 8.9 g of a dark yellow solid; mp 190°–200° C. This material was triturated in hot methanol affording 7.2 g of a yellow solid (71% yield); mp 200°–204° C. (dec.).

Analysis: Calculated for $C_{21}H_{21}ClN_6O_4S$: C, 51.59; H, 4.33; N, 17.19. Found: C, 51.76; H, 4.36; N, 17.25. Spectral data are consistent with the assigned structure.

Step (e): Preparation of Title Product

Reaction was carried out by the method and molar ratios of Step (d) of Example I except that the product of Step (d) herein (0.012 mol) was used in place of the product of Step (c) of Example I. Reaction gave 5.3 g of a beige solid. This material was dissolved in hot methanol (50 ml), treated with 9N ethanolic hydrogen chloride (4 ml) and the resulting solid collected by filtration. Drying of this material under vacuum (<0.05 mm of Hg) at 80° C. for 16 hours gave 3.07 g (49% yield) of 6-chloro-2-[3-[4-(3-cyano-2-pyridinyl)-1-piperazinyl]-propyl]-2,3-dihydro-3-oxo-1H-isoindole-5-sulfonamide hydrochloride hydrated with 0.75 mol of water; mp 252°–255° C. (dec.); a white solid.

Analysis: Calculated for $C_{21}H_{33}ClN_6O_3S$·$HCl$·$0.75H_2O$: C, 48.05; H, 4.90; N, 16.01; $H_2O$, 2.57. Found: C, 47.79; H, 4.82; N, 15.81; $H_2O$, 2.73.

Spectral data are consistent with the assigned structure.

EXAMPLE VII

1-[3-[5-(Aminosulfonyl)-6-chloro-1,3-dihydro-3-oxo-2H-isoindol-2-yl]propyl]-4-benzolpiperazine

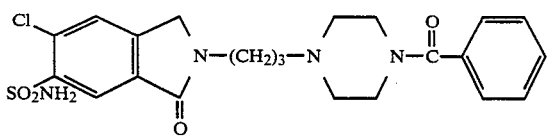

was prepared as the hydrochloride monohydrate in the following steps:

Step (a): Preparation of N-[3-[4-(benzoyl)-1-piperazinyl]propyl]phthalimide

Reaction was carried out by the method and molar ratios of Step (a) of Example II except that 1-benzoyl-piperazine (0.023 mol) was used in place of the 1-(m-chlorophenyl)piperazine. Reaction gave 8.4 g of a yellow solid (98% yield); mp 100°–104° C. Spectral data are consistent with the assigned structure.

Step (b): Preparation of 1-(3-amino-1-propyl)-4-benzoylpiperazine

Reaction was carried out by the method and molar ratios of Step (b) of Example I except that the product of Step (a) of this Example (0.022 mol) was used in place of the product of Step (a) of Example I. Reaction gave 5.25 g of an orange oil (96.5% yield). Spectral data are consistent with the assigned structure. This material was used without further purification.

Step (c): Preparation of 1-[3-[5-(aminosulfonyl)-6-chloro-1,3-dihydro-1,3-dioxo-2H-isoindol-2-yl]propyl]-4-benzoylpiperazine Reaction was carried out by the method and molar ratios of Step (c) of Example I except that the product of Step (b) of this Example (0.021 mol) was used in place of the product of Step (b) of Example I. Reaction afforded a dark yellow solid. This material was collected and triturated with methanolether (1:1) affording 4.1 g of a yellow solid (40% yield); mp 160°–170° C. (dec.). Spectral data are consistent with the assigned structure. This material was used without further purification.

Step (d): Preparation of the Title Product

Reaction was carried out by the method and molar ratios of Step (d) of Example I except that the product of Step (c) of this Example (0.008 mol) was used in place of the product of Step (c) of Example I. Reaction gave 3.1 g of a foamy residue. This material was dissolved in methanol (30 ml), treated with 9N ethanolic hydrogen chloride (5 ml) and the precipitate collected. Drying of this material under vacuum (<0.05 mm of Hg) at 110° C. for 16 hours afforded 1.85 g (45% yield) of 1-[3-[5-(aminosulfonyl)-6-chloro-1,3-dihydro-3-oxo-2H-isoindol-2-yl]propyl]-4-benzoylpiperazine hydrochloride monohydrate; mp 178°–220° C. (dec.); a white solid.

Analysis: Calculated for $C_{22}H_{25}ClN_4O_4S$·$HCl$·$H_2O$: C, 49.72; H, 5.31; N, 10.54; $H_2O$, 3.39. Found: C, 49.88; H, 5.24; N, 10.48; $H_2O$, 4.61.

Spectral data are consistent with the assigned structure.

EXAMPLE VIII

1-[3-[5-(Aminosulfonyl)-6-chloro-1,3-dihydro-3-oxo-2H-isoindol-2-yl]propyl]-4-(4-fluorobenzoyl)piperazine

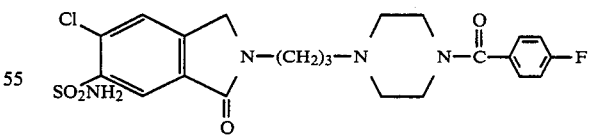

was prepared in the following steps:

Step (a): Preparation of 4-fluorobenzoyl chloride

A mixture of 4-fluorobenzoic acid (0.15 mol), thionyl chloride (0.45 mol) and dimethylformamide (5 drops) in chloroform (200 ml) was heated at reflux for 16 hours. Volatiles were removed from the cooled solution in vacuo. The residue was diluted with carbon tetrachloride (100 ml) and the mixture evaporated in vacuo to remove residual thionyl chloride. The residue was distilled affording 19.7 g of a clear oil (83% yield); bp 110°–112° C. at 40 mm of Hg. Spectral data are consistent with the assigned structure.

Step (b): Preparation of 1-(4-fluorobenzoyl)-piperazine

Concentrated hydrochloric acid was added dropwise to a solution of piperazine (0.124 mol) in water (110 ml) to adjust the pH to 2.8. The solution was then heated to 50° C. 4-Fluorobenzoyl chloride (0.124 mol) was added to the warm solution dropwise while maintaining the pH at 2.8 by the concurrent addition of 40% aqueous sodium acetate solution. After complete addition, a solution of potassium carbonate (47 g) in water (50 ml) was added and the mixture cooled in an ice bath. The cold mixture was extracted with chloroform (5×150 ml). The combined extracts were dried (MgSO₄) and evaporated in vacuo affording 22.5 g of a white solid (88% yield). Spectral data are consistent with the assigned structure. This material was used without further purification.

Step (c): Preparation of N-[3-[4-(4-fluorobenzoyl)-1-piperazinyl]propyl]-phthalimide Reaction was carried out by the method and molar ratios of Step (a) of Example I except that the product of Step (b) of this Example (0.05 mol) was used in place of the 1-(o-methoxyphenyl)piperazine. Reaction gave 22.6 g of a yellow oil (~100% yield). Spectral data are consistent with the assigned structure. This material was used without further purification.

Step (d): Preparation of 1-(3-amino-1-propyl)-4-(4-fluorobenzoyl)piperazine

Reaction was carried out by the method and molar ratios of Step (b) of Example I except that the product of Step (c) herein (0.049 mol) was utilized in place of the product of Step (a) of Example I. Reaction afforded 10.5 g of an orange oil (81% yield). Spectral data are consistent with the assigned structure. This material was used without further purification.

Step (e): Preparation of 1-[3-[5 (aminosulfonyl)-6-chloro-1,3-dihydro-1,3-dioxo-2H-isoindol-2-yl]propyl]-4-(4-fluorobenzoyl)piperazine Reaction was carried out by the method and molar ratios of Step (c) of Example I except that the product of Step (d) herein (0.021 mol) was used in place of the product of Step (b) of Example I. Reaction gave 9.5 g of a tan solid. This material was triturated with methanol affording 7.0 g of a yellow solid (65% yield); mp 185°–188° C. (dec.). Spectral data are consistent with the assigned structure. This material was used without further purification.

Step (f): Preparation of Title Product

Reaction was carried out by the method and molar ratios of Step (d) of Example I except that the product of Step (e) of this Example (0.012 mol) was used in place of the product of Step (c) of Example I. Reaction gave 6.0 g of a foamy residue. This material was triturated in methanol (50 ml) at reflux. Filtration of the cooled mixture and drying of the precipitate under vacuum (<0.05 mm of Hg) at 80° C. for 72 hours afforded 3.7 g (63% yield) of 1-[3-[5-(aminosulfonyl)-6-chloro-1,3-dihydro-3-oxo-2H-isoindol-2-yl]propyl]-4-(4-fluorobenzoyl)piperazine; mp 113°–124° C. (dec.); a white solid.

Analysis: Calculated for $C_{22}H_{24}ClFN_4O_4S$: C, 53.38; H, 4.89; N, 11.32. Found: C, 53.27; H, 4.97; N, 11.28.

Spectral data are consistent with the assigned structure.

EXAMPLE IX

6-Chloro-2,3-dihydro-3-oxo-2-[3-[4-[3-(trifluoromethyl)-phenyl]-1-piperazinyl]propyl]-1H-isoindole-5-sulfonamide

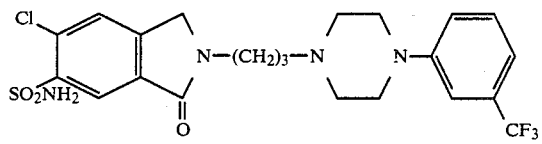

was prepared as the hydrochloride hemihydrate in the following steps:

Step (a): Preparation of N-[3-[4-[3-(trifluoromethyl)phenyl]-1-piperazinyl]-propyl]phthalimide Reaction was carried out by the method and molar ratios of Step (a) of Example I except that 1-[3-(trifluoromethyl)phenyl]piperazine (0.04 mol) was utilized in place of the 1-(o-methoxyphenyl)piperazine of Example I. Reaction afforded 15.8 g of an orange oil (83% yield). Spectral data are consistent with the assigned structure containing a chloroform impurity. This material was used without further purification.

Step (b): Preparation of 1-(3-amino-1-propyl)-4-[3-(trifluoromethyl)phenyl]piperazine Reaction was carried out by the method and molar ratios of Step (b) of Example I except that the product of Step (a) herein (0.033 mol) was used in place of the product of Step (a) of Example I. Reaction afforded 7.9 g of a clear oil (83% yield). Spectral data are consistent with the assigned structure. This material was used without further purification.

Step (c): Preparation of 6-chloro 2,3-dihydro-1,3-dioxo-2-[3-[4-[3-(trifluoromethyl)phenyl]-1-piperazinyl]propyl]-1H-isoindole-5-sulfonamide Reaction was carried out by the method and molar ratios of Step (c) of Example I except that the product of Step (b) of this Example (0.021 mol) was used in place of the product of Step (b) of Example I. Reaction gave 6.6 g of a tan solid (59% yield); mp 185°–190° C. Spectral data are consistent with the assigned structure. This material was used without further purification.

A sample triturated with hot acetonitrile provided pale yellow material, mp 190°–192° C. (dec.).

Analysis: Calculated for $C_{22}H_{22}ClF_3N_4O_4S \cdot 0.4H_2O$: C, 49.10; H, 4.27; N, 10.41; H₂O, 1.34. Found: C, 48.77; H, 4.19; N, 10.58; H₂O, 0.97.

Step (d): Preparation of Title Product

Reaction was carried out by the method and molar ratios of Step (d) of Example I except that the product of Step (c) of this Example (0.011 mol) was used in place of the product of Step (c) of Example I. Reaction gave 4.2 g of an orange solid. This material was dissolved in hot methanol (35 ml), treated with 9N ethanolic hydrogen chloride (3 ml) and allowed to crystallize. The resulting precipitate was collected and dried under vacuum (<0.05 mm of Hg) at 110° C. for 16 hours affording 2.4 g (40% yield) of 6-chloro-2,3-dihydro-3-oxo-2-[3-[4-[3-(trifluoromethyl)phenyl]-1-piperazinyl]propyl]-1H-isoindole-5-sulfonamide hydrochloride hemihydrate; mp 220°–222° C. (dec.); a white solid.

Analysis: Calculated. for $C_{22}H_{24}ClF_3N_4O_3S$ .HCl.0.5H$_2$O: C, 46.98; H, 4.66; N, 9.96; H$_2$O, 1.60. Found: C, 47.14; H, 4.74; N, 9.91; H$_2$O, 1.60.

Spectral data are consistent with the assigned structure.

EXAMPLE X

6-Chloro-2,3-dihydro-3-oxo-2-[3-(4-phenyl-1-piperazinyl)propyl]-1H-isoindole-5-sulfonamide

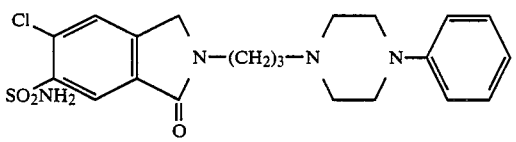

was prepared as the hydrochloride hydrated material in the following steps:

Step (a): Preparation of N-[3-(4-phenyl-1-piperazinyl)propyl]phthalimide

Reaction was carried out by the method and molar ratios of Step (a) of Example I except that N-phenylpiperazine (0.019 mol) was utilized in place of the 1-(o-methoxyphenyl)piperazine of Example I. Reaction afforded 6.03 g of a yellow solid (93% yield); mp 105°–122° C. Spectral data are consistent with the assigned structure.

Step (b): Preparation of 1-(3-amino-1-propyl)-4-phenylpiperazine

Reaction was carried out by the method and molar ratios of Step (b) of Example I except that the product of Step (a) of this Example (0.017 mol) was used in place of the product of Step (a) of Example I. Reaction afforded 3.44 g of a yellow oil (93% yield). Spectral data are consistent with the assigned structure. This material was used withou further purification.

Step (c): Preparation of 6-chloro-2,3-dihydro-1,3-dioxo-2-[3-(4-phenyl-1-piperazinyl)propyl]-1H-isoindole-5-sulfonamide Reaction was carried out by the method and molar ratios of Step (c) of Example I except that the product of Step (b) of this Example (0.015 mol) was used in place of the product of Step (b) of Example I. Reaction gave 5.2 g of a yellow solid (75% yield); mp 90°–130° C. (dec.). A portion (0.55 g) of this material was triturated with acetonitrile affording 0.42 g of a yellow solid; mp 173°–178° C. (dec.).

Analysis: Calculated for $C_{21}H_{23}ClN_4O_4S.0.33H_2O$: C, 53.79; H, 5.09; N, 11.95; H$_2$O, 1.28. Found: C, 54.07; H, 5.07; N, 12.22; H$_2$O, 1.44. Spectral data are consistent with the assigned structure.

Step (d): Preparation of the Title Product

Reaction was carried out by the method and molar ratios of Step (d) of Example I except that the product of Step (c) of this Example (0.01 mol) was used in place of the product of Step (c) of Example I. Reaction gave 2.2 g of a yellow solid. This material was dissolved in methanol (25 ml), treated with 9N ethanolic hydrogen chloride (3 ml) and allowed to crystallize. The resulting precipitate was collected and dried under vacuum (<0.05 mm of Hg) at 110° C. for 16 hours affording 0.95 g (19.5% yield) of 6-chloro-2,3-dihydro-3-oxo-2-[3-(4-phenyl-1-piperazinyl)propyl]-1H-isoindole-5-sulfonamide hydrochloride hydrate; mp 210°–225° C. (dec.); a white solid.

Analysis: Calculated for $C_{21}H_{25}ClN_4O_3S.HCl.0.67H_2O$: C, 50.72; H, 5.54; N, 11.27; H$_2$O, 2.39. Found: C, 50.89; H, 5.45; N, 11.18; H$_2$O, 2.28.

Spectral data are consistent with the assigned structure.

EXAMPLE XI

6-Chloro-2,3-dihydro-2-[4-[4-(2-methoxyphenyl)-1-piperazinyl]butyl]-3-oxo-1H-isoindole-5-sulfonamide

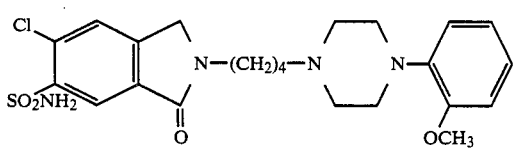

was prepared as follows:

Step (a): Preparation of N-[4-[4-(2-methoxyphenyl)-1-piperazinyl]butyl]-phthalimide Reaction was carried out by the method and molar ratios of Step (a) of Example I except that N-(4-bromobutyl)phthalimide was used in place of N-(3-bromopropyl)phthalimide and except that 0.035 mol of the 1-(o-methoxyphenyl)piperazine was used. Reaction afforded 14.2 g of a yellow oil (~100 yield). Spectral data are consistent with the assigned structure containing a chloroform impurity. This material was used without further purification.

Step (b): Preparation of 1-(4-amino-1-butyl)-4-(2-methoxyphenyl)piperazine

Reaction was carried out by the method and molar ratios of Step (b) of Example I except that the product of Step (a) of this Example (0.035 mol) was used in place of the product of Step (a) of Example I. Reaction gave 10.7 g of a pale yellow oil (~100% yield). Spectral data are consistent with the assigned structure. This material was used without further purification.

Step (c): Preparation of 6-chloro-2,3-dihydro-1,3-dioxo-2-[4-[4-(2-methoxyphenyl)-1-piperazinyl]butyl]-1H-isoindole-5-sulfonamide Reaction was carried out by the method and molar ratios of Step (c) of Example I except that the product of Step (b) of this Example (0.021 mol) was used in place of the product of Step (b) of Example I. Reaction gave 6.1 g of a yellow solid. This material was triturated with acetonitrile (25 ml) affording 4.7 g of a pale yellow solid (44% yield); mp 205°–250° C. (dec.). Spectral and analytical data are consistent with the assigned structure.

Step (d): Preparation of Title Product

Reaction was carried out by the method and molar ratios of Step (d) of Example I except that the product of Step (c) of this Example (0.009 mol) was used in place of the product of Step (c) of Example I. Reaction gave 2.94 g of a beige solid. This material was triturated with methanol (10 ml) affording 2.10 g (48.8% yield) of 6-chloro-2,3-dihydro-2-[4-[4-(2methoxyphenyl)-1-piperazinyl]butyl]-3-oxo-1H-isoindole-5-sulfonamide; mp 197°–203° C. (dec.); a beige solid.

Analysis: Calculated for $C_{23}H_{29}ClN_4O_4S$: C, 56.03; H, 5.93; N, 11.36. Found: C, 56.13; H, 6.06; N, 11.23.

Spectral data are consistent with the assigned structure.

EXAMPLE XII

6-Chloro-2,3-dihydro-2-[3-[4-(3-fluoro-6-methoxyphenyl)-1-piperazinyl]prooyl]-3-oxo-1H-isoindole-5-sulfonamide

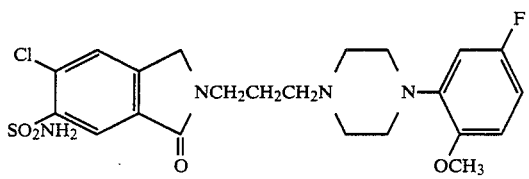

was prepared in the following steps:

Step (a): Preparation of 1-fluoro-3-nitro-4-methoxybenzene

Fuming nitric acid (90%, 0.36 mol) was added to a mixture of 1-fluoro-4-methoxybenzene (0.3 mol), glacial acetic acid (1 mol) and acetic anhydride (0.4 mol) at 0o The reaction mixture was permitted to warm to room temperature and after one hour was poured in ice water yielding 31 g (61%) of 1-fluoro-nitro-4-methoxybenzene.

Step (b): Preparation of 5-fluoro-2-methoxyaniline

Reduction of 1-fluoro-3-nitro-4-methoxybenzene (34 g) in 400 ml of ethanol was carried out with 2 g of 10% palladium/carbon catalyst in hydrogen. The mixture was filtered, concentrated and used without further purification.

Step (c): Preparation of 1-(3-fluoro-6-methoxyphenyl)piperazine 5-fluoro-2-methoxyaniline (0.092 mol) and bis(2-chloroethyl)aminehydrochloride (0.1 mol) in xylene (300 ml) was refluxed with stirring for a period of 20 hrs. Water was added to the reaction and the organic layer discarded. The aqueous layer was basified with sodium hydroxide and extracted with methylene chloride (2×100 ml). The methylene chloride extract was dried (sodium carbonate), filtered, and concentrated. Residual material was distilled to provide 8.8 g (45% yield) of piperazine product, b.p. 111°–114° C. 0.15 mmHg:

Step (d): Preparation of N-[3-[4-(3-fluoro-6-methoxyphenyl)-1-piperazinyl]propyl]-phthalimide Reaction was carried out by the method and molar ratios of Step (a) of Example I except that 1-(3-fluoro-6-methoxyphenyl)piperazine (0.042 mol) was used in place of the 1-(o-methoxyphenyl)piperazine. Reaction gave 16.7 g (about 100%) of phthalimide intermediate.

Step (e): Preparation of 1-(3-amino-1-propyl)-4-(3-fluoro-6-methoxyphenyl)piperazine Reaction was carried out by the method and molar ratios of Step (b) of Example I except that the product of Step (d) herein (0.012 mol) was utilized in place of the product of Step (a) of Example I. Reaction afforded 2.7 g (82%) of the amino intermediate. This material was used without further purification.

Step (f): Preparation of 6-chloro-2,3-dihydro-2-[3-[4-(3-fluoro-6-methoxyphenyl)-1-piperazinyl]propyl]-1,3-dioxo-1H-isoindole-5-sulfonamide Reaction was carried out by the method and molar ratios of step (c) of Example I except that the product of step (e) herein (0.042 mol) was utilized in place of the product of step (b) of Example I. Reaction gave 16.7 g (100%) of the 1,3-dioxo intermediate used without further purification.

Step (g): Preparation of Title Product

Reaction was carried out by the method and molar ratios of Step (d) of Example I except that the product of Step (f) herein (0.015 mol) was utilized in place of the product of Step (c) of Example I. The crude product (6.3 g) was taken up in methanol and the hydrochloride salt prepared. The hydrochloride salt was dissolved in methanol and treated with saturated sodium bicarbonate solution to provide the free base. The mixture was refluxed for 5 minutes and water added. The solid obtained was collected, taken up in the methylene chloride, dried (MgSO ), filtered and concentrated to provide 1.6 g of 6-chloro-2,3-dihydro-2-[3-[4-(3-fluoro-6-methoxyphenyl)-1-piperazinyl]propyl]-3-oxo-1H-isoindole-5-sulfonamide, m.p. 158°–163° C.

Analysis: Calculated for $C_{22}H_{26}ClFN_4O_4S$: C, 53.17; H, 5.27; N, 11.27. Found: C, 53.52; H, 5.52; N, 11.38.

EXAMPLE XIII

6-Chloro-2,3-dihydro-2-[3-[4-(4-fluoro-2-methoxyohenyl)-1-piperazinyl]propyl]-3-oxo-1H-isoindole-5-sulfonamide

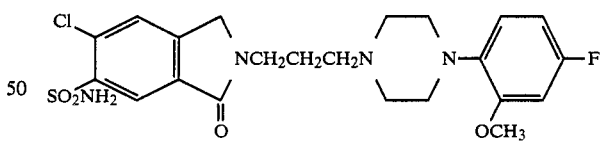

was prepared in the following steps:

Step (a): Preparation of 5-fluoro-2-methoxyaniline

Reduction of 1-fluoro-3-methoxy-4-nitrobenzene (0.11 mol) (prepared by methylation of 5-fluoro-2-nitrophenol with methyl iodide was carried out according to Step (b) of Example XII to provide 14.8 g (98% yield) of 5-fluoro-2-methoxyaniline used without further purification.

Step (b): Preparation of 1-(4-fluoro-2-methoxyphenyl)piperazine

Reaction of bis(2-chloroethyl)amine hydrochloride (0.11 mol) with 5-fluoro-2-methoxyaniline (0.01 mol) according to Step (c) of Example XII, provided 19.5 g (95% yield) of the piperazine intermediate used without further purification.

Step (c): Preparation of N-[3-[4-(4-fluoro-2-methoxyphenyl)-1-piperazinyl]-propyl]-phthalimide Reaction is carried out by the method and molar ratios of Step (a) of Example I except that 1-(4-fluoro-2-methoxyphenyl)piperazine (0.05 mol) was used in place of the 1-(o-methoxyphenyl)piperazine. Reaction gave 18.1 g (96%) of orange-brown oil used without further purification.

Step (d): Preparation of 1-(3-amino-1-propyl)-4-(4-fluoro-2-methoxvphenyl)piperazine Reaction was carried out by the method and molar ratios of Step (b) of Example I except that the product of Step (c) herein was employed in place of the product of Step (a) of Example I. Reaction gave 10.4 g (86%) of amber-orange oil used without further purification.

Step (e): Preparation of 6-chloro-2,3-dihydro-2-[3-[4-(4-fluoro-2-methoxyrhenyl)-1-piperazinyl]propyl]1,3-dioxo-1H-isoindole-5-sulfonamide Reaction was carried out by the method and molar ratios of Step (c) of Example I except that the product of Step (b) herein was employed in place of the product of Step (a) of Example I. The reaction product was stirred with n-heptane and filtered to provide 16.7 g (45%) of the 1-3,dioxoisoindole intermediate, mp 100°–115° C. used without further purification.

Step (f): Preparation of Title Product

Reaction was carried out by the method and molar ratios of Step (d) of Example I except the product of Step (e) herein (0.03 mol) was utilized in place of the product of Step (c) of Example I. Crystallization of the crude product from ethyl acetate provided 6.14 g (42%) of 6-chloro-2,3-dihydro-2-[3-[4-(4-fluoro-2-methoxyphenyl)-1-piperazinyl]propyl]-3-oxo-1H-isoindole-5-sulfonamide, mp 205°–209° C. (dec.).

Analysis: Calculated for $C_{22}H_{26}ClFN_4O_4S$: C, 53.17; H, 5.27; N, 11.27. Found: C, 53.24; H, 5.42; N, 11.60.

EXAMPLE XIV

The compounds synthesized in Examples I–XI were tested for diuretic acrivity. The compound of Example I was tested as its monohydrochloride 2-propanolate hydrate, i.e. as $C_{22}H_{27}ClN_4O_4S\cdot HCl\cdot 0.2(CH_3)_2CHOH\cdot 0.15H_2O$. Testing was carried out by the diuretic screen of Lipschitz, et al. described previously. In Table I below Volume Ratio is the ratio of total volume excreted for the test comuound compared to the total volume excreted for the control, Na+Ratio is the Na+ excreted for the test compound compared to the Na+excreted for the control, K+Ratio is the K+excreted for the test compound compared to the K+excreted for the control. Female Sprague Dawley rats were used in Test Nos. 1, 2, 6, 7, 11–29. Male Okamoto-Aoki rats were used in Test Nos. 3–5 and 8–10 and testing for antihypertensive activity was carried out simultaneously on the Test Nos. 3–5 rats. In some instances, compounds were retested at the same dose level. Test results were as follows:

TABLE I

| Test No. | Compound | Dose mg/kg | Volume Ratio | Na+ Ratio | K+ Ratio | Urinary Na/K (Test Compound) | Urinary Na/K (Control) |
|---|---|---|---|---|---|---|---|
| 1 | Example I | 3 | 0.93 | 1.08 | 1.00 | 2.55 | 2.37 |
| 2 | Example I | 30 | 0.98 | 1.36 | 1.06 | 2.98 | 2.37 |
| 3 | Example I | 0.3 | 0.82 | 0.96 | 0.78 | 0.81 | 0.71 |
| 4 | Example I | 3.0 | 2.04 | 1.68 | 1.03 | 1.14 | 0.71 |
| 5 | Example I | 30 | 2.51 | 2.61 | 1.17 | 1.56 | 0.71 |
| 6 | Example II | 30 | 1.17 | 1.43 | 1.29 | 3.41 | 3.01 |
| 7 | Example III | 30 | 1.16 | 1.34 | 1.16 | 3.44 | 3.01 |
| 8 | Example III | 3 | 1.22 | 1.13 | 1.21 | 6.1 | 6.4 |
| 9 | Example III | 10 | 1.26 | 1.16 | 1.15 | 6.7 | 6.4 |
| 10 | Example III | 30 | 1.63 | 1.35 | 1.30 | 6.7 | 6.4 |
| 11 | Example IV | 30 | 0.72 | 1.21 | 1.17 | 3.15 | 3.05 |
| 12 | Example IV | 3 | 1.04 | 1.23 | 0.97 | 3.49 | 2.73 |
| 13 | Example IV | 30 | 0.93 | 1.33 | 1.26 | 2.98 | 2.73 |
| 14 | Example V | 3 | 1.28 | 1.45 | 0.89 | 3.34 | 2.10 |
| 15 | Example V | 30 | 2.20 | 2.71 | 1.33 | 4.14 | 2.10 |
| 16 | Example V | 0.3 | 0.89 | 0.97 | 0.99 | 2.33 | 2.56 |
| 17 | Example V | 3 | 1.17 | 1.31 | 1.15 | 2.74 | 2.56 |
| 18 | Example VI | 3 | 1.53 | 1.69 | 0.98 | 3.55 | 2.06 |
| 19 | Example VI | 30 | 1.74 | 2.04 | 1.11 | 3.90 | 2.06 |
| 20 | Example VII | 3 | 0.89 | 0.92 | 1.13 | 2.07 | 2.51 |
| 21 | Example VII | 30 | 1.12 | 1.40 | 1.11 | 3.27 | 2.51 |
| 22 | Example VIII | 3 | 0.89 | 0.98 | 0.94 | 2.60 | 2.51 |
| 23 | Example VIII | 30 | 1.22 | 1.42 | 0.99 | 3.69 | 2.51 |
| 24 | Example IX | 3 | 1.02 | 1.27 | 1.06 | 2.99 | 2.56 |
| 25 | Example IX | 30 | 1.84 | 2.12 | 1.40 | 3.67 | 2.56 |
| 26 | Example X | 3 | 1.24 | 1.38 | 1.21 | 3.19 | 2.89 |
| 27 | Example X | 30 | 1.53 | 1.63 | 1.57 | 2.83 | 2.89 |
| 28 | Example XI | 3 | 1.08 | 1.13 | 1.11 | 3.09 | — |
| 29 | Example XI | 30 | 0.94 | 1.17 | 1.37 | 2.62 | — |

The testing indicated that all the compounds of Examples I–XI possess diuretic (total volume) and/or natriuretic activity.

EXAMPLE XV

Testing was carried out on the compounds of Examples I–XII for antihypertensive activity. In the case of all the compounds testing was carried out on the Spontaneously Hypertensive rat as described hereinbefore. In the case of the compounds of Examples I–IV testing was also carried out on the DOCA-salt Hypertensive Rat. The compound of Example I was tested as its monochloride 2-propanolate hydrate, i.e. as $C_{22}H_{27}ClN_4O_4S\cdot HCl\cdot 0.2(CH_3)_2CHOH\cdot 0.15H_2O$ in Tests 1–5; and as the ¾ mole hydrochloride, i.e. $C_{22}H_{27}ClN_4O_4S$: 3/4 HCl in Tests 3a, 4a, 5a–5d. Test results are set forth in Table II below wherein SHR stands for Spontaneously Hypertensive rat, DOCA stands for DOCA-salt Hypertensive Rat, ΔBP stands for the change in systolic blood pressure in mm Hg, ΔHR stands for the change in mean heart rate in beats per minute and the times set forth are the times after dosing. A peak change in ΔBP of more than 20 is considered as indicating activity.

TABLE II

| Test No. | Compound | Dose mg/kg | Type Rat | ΔBP 2 hours | ΔHR 2 hours | ΔBP 4 hours | ΔHR 4 hours |
|---|---|---|---|---|---|---|---|
| 1 | Example I | 30 | SHR | −84 ± 10 | 16 ± 15 | −52 ± 13 | 4 ± 17 |
| 2 | Example I | 0.3 | SHR | | | −18 ± 6 | 11 ± 3 |
| 3 | Example I | 3.0 | SHR | | | −43 ± 7 | 10 ± 15 |

TABLE II-continued

| Test No. | Compound | Dose mg/kg | Type Rat | ΔBP 2 hours | ΔHR 2 hours | ΔBP 4 hours | ΔHR 4 hours |
|---|---|---|---|---|---|---|---|
| 3a | Example I | 3.0 | SHR | −23 ± 8 | 8 ± 10 | −10 ± 5 | 14 ± 18 |
| 4 | Example I | 30 | SHR | | | −84 ± 6 | 26 ± 10 |
| 4a | Example I | 30 | SHR | −97 ± 10 | 16 ± 8 | −52 ± 13 | 2 ± 9 |
| 5 | Example I | 30 | DOCA | | | −49 ± 9 | 59 ± 28 |
| 5a | Example I | 0.3 | DOCA | | | −14 ± 5 | −8 ± 20 |
| 5b | Example I | 3.0 | DOCA | | | −15 ± 6 | −6 ± 24 |
| 5c | Example I | 30 | DOCA | | | −53 ± 9 | 53 ± 26 |
| 5d | Example I | 100 | DOCA | | | −75 ± 3 | 23 ± 32 |
| 6 | Example II | 30 | SHR | −23 ± 4 | −18 ± 10 | −18 ± 7 | −4 ± 16 |
| 7 | Example II | 30 | DOCA | | | −33 ± 5 | 22 ± 17 |
| 8 | Example III | 30 | SHR | −47 ± 14 | 10 ± 3 | −69 ± 20 | 10 ± 10 |
| 9 | Example III | 30 | DOCA | | | −62 ± 13 | 63 ± 32 |
| 10 | Example IV | 30 | SHR | −48 ± 19 | −36 ± 5 | −53 ± 7 | −22 ± 22 |
| 11 | Example IV | 0.3 | DOCA | | | −8 ± 3 | 13 ± 21 |
| 12 | Example IV | 3 | DOCA | | | −31 ± 7 | 22 ± 9 |
| 13 | Example IV | 30 | DOCA | | | −79 ± 4 | 18 ± 13 |
| 14 | Example V | 30 | SHR | −27 ± 10 | −6 ± 15 | −30 ± 14 | −39 ± 14 |
| 15 | Example VI | 30 | SHR | −17 ± 10 | 6 ± 41 | −7 ± 11 | −10 ± 18 |
| 16 | Example VII | 30 | SHR | −7 ± 8 | −32 ± 14 | −14 ± 3 | −74 ± 24 |
| 17 | Example VIII | 30 | SHR | −9 ± 5 | 2 ± 15 | −9 ± 4 | 24 ± 15 |
| 18 | Example IX | 30 | SHR | −34 ± 14 | 6 ± 17 | −32 ± 10 | 0 ± 14 |
| 19 | Example X | 30 | SHR | (peak change at 2 hours in ΔBP of −34 mm Hg) | | | |
| 20 | Example XI | 30 | SHR | −94 ± 10 | −2 ± 8 | −60 ± 21 | −22 ± 14 |
| 21 | Example XII | 30 | SHR | (peak change at 2 hours in ΔBP of −64 mm Hg) | | | |

This testing indicates that the compounds of Examples I, II, III, IV, V, IX, X, XI and XII have good antihypertensive effect without significantly affecting heart rate.

EXAMPLE XV

In this example the compounds of Examples I (modified), II, III, V, VI, VII, VIII, IX and XI were tested in rats for in vivo α blocking activity according to methodology described at page 312 of Deitchman, et al., Journal of Pharmacological Methods, 3, 311–321 (1980). In this test phenylephrine (PE below) or norepinephrine (NE below) was administered as an α-agonist to the rats before and after dosing with the test drug and the average interpolated dose or PE/NE effecting a 50 mm Hg increase in mean arterial blood pressure was determined. Table III below records the results. In such Table, $ED_{50}$ stands for such average interpolated dose and Average Dose Shift stands for the average ratio of $ED_{50}$ after drug administration to $ED_{50}$ before drug administration. The compound of Example I was tested as its monochloride 2-propanolate hydrate, i.e. as $C_{22}H_{27}ClN_4O_4S \cdot HCl \cdot 0.2(CH_3)_2CHOH \cdot 0.15H_2O$ in Tests 1–5 and as the ¾ mole hydrochloride, i.e. $C_{22}H_{27}ClN_4O_4S \cdot \tfrac{3}{4}HCL$ in Tests 2a and 3a. The route was intravenous except in the case of the runs of Test Nos. 2a, 3, 3a, 26–29 the route was oral.

Prazosin (0.03 mg/kg, i.v.) causes a dose shift of approximately 30 in response to PE, and a shift of 5–10 in response to NE.

TABLE III

| Test No. | Compound | Dose | Antagonist | $ED_{50}$ | Average Dose Shift |
|---|---|---|---|---|---|
| 1 | Example I | 0.3 | PE | 35.25 | 11 ± 2 |
| 2 | Example I | 1.0 | PE | 161.8 | 68 ± 8 |
| 2a | Example I | 10 | PE | 24.7 | 9 ± 2 |
| 3 | Example I | 30 | PE | 98.5 | 33 ± 11 |
| 3a | Example I | 30 | PE | 99 | 34 ± 3 |
| 4 | Example I | 0.3 | NE | 1.3 | 3 ± 0.3 |
| 5 | Example I | 1.0 | NE | 5.6 | 11 ± 1 |
| 6 | Example II | 0.1 | PE | 4.4 | 2 |
| 7 | Example II | 1.0 | PE | 34.0 | 12 ± 0.3 |
| 8 | Example II | 10 | PE | >300 | >200 |
| 9 | Example III | 0.1 | PE | 4.24 | 2.2 |
| 10 | Example III | 1.0 | PE | 41.0 | 15 ± 0.4 |
| 11 | Example III | 10 | PE | >65 | dose too high |
| 12 | Example V | 10 | PE | 4.8 | 1.7 ± 0.3 |
| 13 | Example VI | 1.0 | PE | 9.8 | 3 ± 0.2 |
| 14 | Example VI | 10 | PE | 113.5 | 27 ± 3 |
| 15 | Example VII | 10 | PE | 2.6 | >1.0 |
| 16 | Example VIII | 10 | PE | 4.2 | 1 ± 0.1 |
| 17 | Example IX | 1.0 | PE | 11.3 | 2.2 |
| 18 | Example IX | 10 | PE | 17.7 | 6 ± 0.6 |
| 19 | Example XI | 0.1 | PE | 15.1 | 4 ± 0.3 |
| 20 | Example XI | 0.3 | PE | 68.4 | 21 ± 3 |
| 21 | Example XI | 0.5 | PE | 143.25 | 46 ± 6 |
| 22 | Example XI | 1.0 | PE | 375 | 114 |
| 23 | Example XI | 0.3 | NE | 0.98 | 5 ± 0.5 |
| 24 | Example XI | 1 | NE | 6.85 | 27 ± 28 |
| 25 | Example XI | 3 | NE | 11.8 | 63 ± 19 |
| 26 | Example XI | 10 | PE | 19.6 | 7 ± 0.4 |
| 27 | Example XI | 30 | PE | 122 | 44 ± 14 |
| 28 | Example XI | 10 | PE | 12.4 | 3 ± 0.6 |
| 29 | Example XI | 30 | PE | 105 | 29 ± 3.8 |
| 30 | Example X | 1 | PE | 45.0 | 13 ± 2 |

The above results indicate that the compounds of Examples I, II, III, VI, X and XI are active as in vivo α blockers and that the compound of Example IX is weakly active.

EXAMPLE XVI

In this Example the compound of Example I as the hydrochloride salt containing ¾ mol of HCl instead of 1 mol HCl, i.e. $C_{22}H_{27}ClN_4O_4S \cdot \tfrac{3}{4}HCl$ referred to hereinafter as MJ 15037-1A, was compared to prazosin, an antihypertensive with α-blocking activity, in respect to diuretic properties.

Studies were conducted with conscious, 150–200 g, female Sprague-Dawley rats (Charles River Labs, Wilmington, MA) using the protocol of Hanson et al., Mineral Elect. Metab., 8: 314–324 (1982). Animals were maintained in stainless steel gang cages in temperature-controlled rooms with a 12-hour light, 12-hour dark cycle and provided Purina Rodent Lab Chow, with water ad libitum. All animals were fasted 18 hours prior to acute (first-day) dosing and water was withheld during the experiment. In the experiment the dose for MJ15037-1A was 3.0 mg/kg, and the dose for prazosin was 0.3 mg/kg. Groups of ten animals (2/cage) were studied. A controlled (non-drug) group comprised of an equal number of animals was included.

Test drugs were suspended in 0.25% methocel-saline (0.9% NaCl) and administered orally by stomach intubation at the doses mentioned above. The oral fluid load volume containing the respective drug dose was uniformly maintained at 25 ml/kg; controls received in methocel-saline vehicle only. Urine was collected over a 5-hour period from rats housed in metabolism cages (2 rats per cage); one specimen consisted of the pooled sample collected from each cage. The urine volume (ml) excreted by each pair of rats was measured and electrolyte (Na, K, Cl, Ca, P) concentrations were determined with an AAII Autoanalyzer (Technicon) employing established procedures. At the end of the acute (1-day) phase, each pair of rats was returned to a separate cage (2/cage) and provided both food and water.

On the following three days, each animal received its respective drug methocel-saline load via a stomach intubation. On the fifth day (after an 18-hour fast) all rats were again treated and placed in metabolism cages (2 rats/cage) for a 5-hour urine collection (chronic-effect: 5-day).

MJ15037-1A (3.0 mg/kg, by mouth) had no natriuretic/diuretic activity after acute treatment (1-day) but after chronic administration (5-days) natriuresis and chlorouresis was observed (32 and 31% increase over control). Prazosin resulted in antidiuresis (significant decreases over control of volume, Na and Cl excretion at 0.3 mg/kg, by mouth).

EXAMPLE XVII

In this Example the compounds of Examples I–XI were tested in vitro for $\alpha_1$ and $\alpha_2$ binding. The compound of Example I was tested as its monochloride 2-propanolate hydrate, i.e. as $C_{22}H_{27}ClN_4O_4S$ .HCl.0.2(CH$_3$)$_2$CHOH 0.15H$_2$O.

In the testing specific brain tissues were prepared as sources of binding sites. Aliquots of the washed membners are incubated with a low concentration of the compound of interest. After incubation at suitable temperature, the reaction mixture is treated to separate the membrane-bound radioligand Radioactivity is measured. Linear regression analysis of the probit value for the percent of binding occurring in the presence of varying concentrations of the compound of interest plotted against the concentration of the compound yields concentrations which inhibit 50% specific binding, the IC$_{50}$. The assay buffer is 50 mM Hepes.KOH, pH 7.4. The ligand is [$^3$H]WB-4101 from New England Nuclear for $\alpha_1$ and [$^3$H]Clonidine from New England Nuclear for $\alpha_2$. The results are considered against phentolamine methanesulfonate (Reference) which is considered a good $\alpha$-binder.

The results are set forth in Table IV below:

TABLE IV

| Test No. | Compound | $\alpha_1$ Binding IC$_{50}$(nM) | $\alpha_2$ Binding IC$_{50}$(nM) | Reference IC$_{50}$(nM) |
| --- | --- | --- | --- | --- |
| 1 | Example I | 1.48 | | 1.11 |
| 2 | Example I | | 555 | 8.6 |
| 3 | Example II | 7.62 | | 3.68 |
| 4 | Example II | | 694 | 5.45 |
| 5 | Example III | 23.4 | | 3.68 |
| 6 | Example III | | 806 | 5.45 |
| 7 | Example IV | 4.16 | | 6.03 |
| 8 | Example IV | | 1434 | 6.71 |
| 9 | Example V | 933 | | 3.47 |
| 10 | Example V | | 1784 | 5.39 |
| 11 | Example VI | 305 | | 4.76 |
| 12 | Example VI | | 3331 | 6.14 |
| 13 | Example VII | 152,321 | | 3.47 |
| 14 | Example VII | | >1000 | 3.12 |
| 15 | Example VIII | 144,463 | | 3.47 |
| 16 | Example VIII | | >1000 | 3.12 |
| 17 | Example IX | 108 | | 4.76 |
| 18 | Example IX | | >1000 | 3.12 |
| 19 | Example X | 16 | | 4.53 |
| 20 | Example X | | 666 | 5.16 |
| 21 | Example XI | 0.4 | | 3.88 |
| 22 | Example XI | 1.89 | | 6.26 |

The above indicate that the compounds of Examples I, II, III, IV, X and XI have $\alpha_1$ binding activity and the compounds of Examples I, II, III and X have $\alpha_2$ binding activity.

EXAMPLE XVIII

Other compounds as follows are prepared by substituting the appropriate piperazine for the 1-(o-methoxyphenyl)piperazine in Example 1.

These compounds have the structural formula I with X equal to Cl wherein

| Example No. | Y | R$_1$ | R$_2$ | R$_3$ |
| --- | --- | --- | --- | --- |
| XVIII-1 | substituted phenyl | cyano | H | H |
| XVIII-2 | substituted phenylalkyl | CH$_3$ | H | H |
| XVIII-3 | substituted phenylalkyl | OCH$_3$ | H | H |
| XVIII-4 | substituted phenylalkyl | CF$_3$ | H | H |
| XVIII-5 | substituted phenylalkyl | OCH$_2$H$_5$ | F | H |
| XVIII-6 | substituted phenylcarbonyl | Cl | H | H |
| XVIII-7 | substituted phenylcarbonyl | OCH$_3$ | H | H |
| XVIII-8 | substituted phenylcarbonyl | C$_3$H$_7$ | H | H |
| XVIII-9 | substituted phenylcarbonyl | CF$_3$ | H | H |
| XVIII-10 | substituted 2-pyridinyl | H | H | H |

These compounds have diuretic and/or natriuretic utility.

EXAMPLE XIX

Compounds are prepared similar to those of Examples I–XIII except having CF$_3$ in place of Cl for X in Formula I by substituting an equimolar amount of 4-trifluoromethyl-5-sulfamoylphthalimide for the 4-chloro-5-sulfamoylphthalimide. For example, 2,3-dihydro-2-[3-[4-(2-methoxyphenyl)-1-piperazinyl]-propyl]-3-oxo-6-trifluoromethyl-1H-isoindole-5-sulfonamide is prepared by making such substitution in Example 1.

These compounds have diuretic and/or natriuretic utility.

EXAMPLE XX

Preparation of 6-chloro-2,3-dihydro-2-[3-[4-(2-methoxyphenyl)-1-piperazinyl]propyl]-3-oxo-1H-isoindole-5-sulfonaide The Title Product of Example I can also be obtained as follows.

Step (a): Preparation of 4-chloro-2-methylbenzoic acid (2)

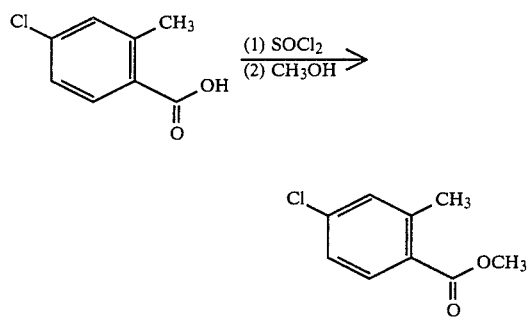

A solution of 85 g (0.5 mol) of 4-chloro-2-methylbenzoic acid (1) (prepared by diazotization of 4-chloro-2-methylaniline and displacement of the diazonium salt with cuprous cyanide forming the nitrile which was hydrolyzed to the acid) and 1 ml of dimethylformamide in 250 ml of thionyl chloride was refluxed for 2 hrs. The solvent was removed under reduced pressure. The resulting residue was poured into 250 ml of methanol and stirred overnight. Methanol was removed under reduced pressure, leaving 83.2 g (90% yield) of pale, yellow liquid (2).

Step (b): Preparation of methyl 4-chloro-5-chlorosulfonyl-2-methylbenzoate (3)

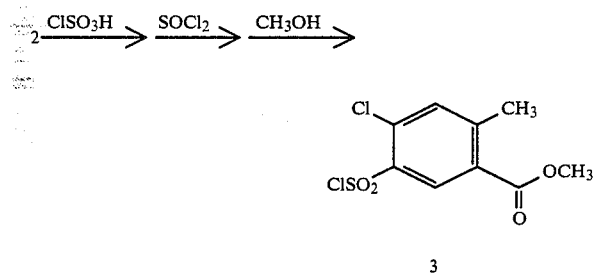

A mixture of 15.8 g (0.086 mol) of methyl 4-chloro-2-methylbenzoate (2) and 25.8 ml (45.2 g, 0.39 mol) of chlorosulfonic acid was heated to a gentle reflux under nitrogen. After 3 hrs., the mixture was cooled and poured slowly into an ice-water mixture. After stirring for 1 hr., the mixture was filtered and rinsed well with ice cold water. Drying in a vacuum oven (60° C.) gave 17.4 g (0.065 mol, 75% yield) of the sulfonylated acid (off-white crystals). A mixture of 14.5 g of the acid and 2 drops of dimethylformamide in 50 ml of thionyl chloride was heated to reflux under nitrogen. After 1½ hrs., the solvent was removed under reduced pressure. Methanol (125 ml) was added to residue material and the solution was cooled to 10° C. After 5 hrs., the solid was filtered and airdried, giving 12.8 g of off-white crystals (3); m.p. 94.5°–96° C.

Step (c): Preparation of methyl 5-aminosulfonyl-2-bromomethyl-2-chlorobenzoate (4)

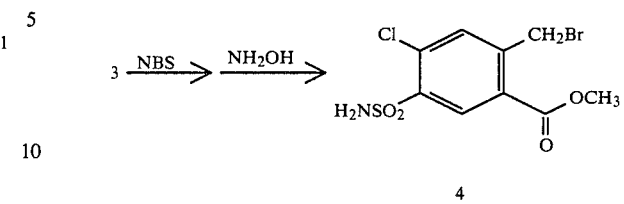

A mixture of 12.0 g (0.042 mol) of 3, 15.1 g (0.085 mol) of N-bromosuccinimide and 0.5 g of 2,2'-azobis(2-methylpropionitrile) in 75 ml of carbon tetrachloride was heated to reflux under nitrogen. Every 2 hrs., the reaction mixture was checked by NMR to determine the ratio of starting material to desired product. The highest ratio obtained was 35:65 of starting material to desired product. When the mixture was further reacted, the product decomposed. After the reaction was checked by NHR, an additional 0.3 g of 2,2'-azobis-(2-methylpropionitrile) was added. After the desired ratio was obtained, the mixture was cooled to room temperature. The mixture was filtered and the filtrate was concentrated under vacuum to give an oil which was used for the next step without purification. This oil was dissolved in 200 ml of a mixture of 3:1 methanol:tetrahydrofuran. After cooling to 0° C. a solution of 5.0 ml of concentrated ammonium hydroxide solution in 50 ml of water was added. After 5 min., the solution was acidified with 30 ml of 10% hydrochloric acid solution. The organic solvents were partially removed under vacuum, then 250 ml of water was added. The solid was filtered and dried, giving 4.0 g (0.012 mol, 28% yield) of white powder. This was a mixture of the desired intermediate (4) with non-brominated material as shown by NMR.

Step (d): Preparation of Title Product

A mixture of 1.0 g (2.9 mmol) of crude 4, anhydrous potassium carbonate (3.6 mmol) and 1-(3-amino-1-propyl)-4-(2-methoxyphenyl) piperazine (3.6 mmol) in 17 ml of acetonitrile is stirred at room temperature under nitrogen until reaction is complete to provide 6-chloro-2,3-dihydro-2-[3-[4-(2-methoxyphenyl)-1-piperazinyl]propyl]-3-oxo-1H-isoindole-5-sulfonamide isolated and purified as described in Example I herein.

Other variations will be evident to those skilled in the art. Therefore, the scope of the invention is intended to be defined by the claims.

What is claimed is:

1. A compound of the Formula I:

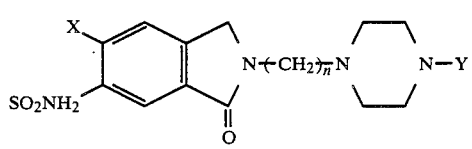

wherein
x is halogen or trifluoromethyl
n is an integer ranging from 2 to 5
y is

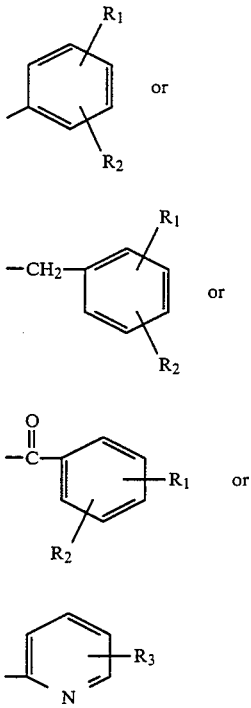

in which
R₁ is hydrogen, halogen, lower alkyl, lower alkoxy, trifluoromethyl, cyano,
R₂ is hydrogen, halogen, lower alkyl, lower alkoxy,
R₃ is hydrogen, cyano,
or pharmaceutically acceptable salts thereof.

2. The compound or salt of claim 1 wherein, in Formula I, X is halogen, n ranges from 2 to 4, Y is (a), R₁ is hydrogen or halogen and R₂ is hydrogen, lower alkyl or lower alkoxy.

3. The compound or salt of claim 2 wherein X is chlorine and R₁ is hydrogen.

4. The compound or salt of claim 3 wherein R₂ is lower alkoxy.

5. The compound or salt of claim 4 wherein R₂ is methoxy.

6. The compound or salt of claim 5 wherein n is 3.

7. The compound of claim 1 which is 6-chloro-2,3-dihydro-2-[3-[4-(2-methoxyphenyl)-1-piperazinyl]-propyl]3-oxo-1H-isoindole-5-Sulfonamide.

8. The compound of claim 1 which is 6-chloro-2-[3-[4-(3-chlorophenyl)-1-piperazinyl]propyl]-2,3-dihydro-3-oxo-1H-isoindole-5-sulfonamide.

9. The compound of claim 1 which is 6-chloro-2,3-dihydro-2-[2-[4-(2-methoxyphenyl)-1-piperazinyl]-ethyl]-3-oxo-1H-isoindole-5-sulfonamide.

10. The compound of claim 1 which is 6-chloro-2,3-dihydro-2-[3-[4-(2-methylphenyl)-1-piperazinyl]-propyl]-3-oxo-1H-isoindole-5-sulfonamide.

11. The compound of claim 1 which is 6-chloro-2,3-dihydro-3-oxo-2-[3-[4-(phenylmethyl)-1-piperazinyl]-propyl]-1Hisoindole-5-sulfonamide.

12. The compound of claim 1 which is 6-chloro-[3-[4-(3-cyano-2-pyridinyl)-1-piperazinyl]propyl]-2,3-dihydro-3-oxo-1H-isoindole-5-sulfonamide.

13. The compound of claim 1 which is 1-[3-[5-(aminosulfonyl)-6-chloro-1,3-dihydro-3-oxo-2H-isoindol-2-yl]propyl]-4-benzoylpiperazine.

14. The compound of claim 1 which is 1-[3-[5-(aminosulfonyl)-6-chloro-1,3-dihydro-3-oxo-2H-isoindol-2-yl]propyl]-4-(4-fluorobenzoyl)piperazine.

15. The compound of claim 1 which is 6-chloro-2,3-dihydro-3-oxo-2-[3-[4-[3trifluoromethyl)phenyl]-1-piperazinyl]propyl]-1H-isoindole-5-sulfonamide.

16. The compound of claim 1 which is 6-chloro-2,3-dihydro-3-oxo-2-[3-(4-phenyl-1-piperazinyl)pronyl]-1H-isoindole-5-sulfonamide.

17. The compound of claim 1 which is 6-chloro-2,3-dihydro-2-[4-[4-(2-methoxyphenyl)-1-piperazinyl]-butyl]-3-oxo-1H-isoindole-5-sulfonamide.

18. The compound of claim 1 which is 6-chloro-2,3-dihydro-2-[3-[4-(3-fluoro-6-methoxyphenyl)-1-piperazinyl]propyl]-3-oxo-1H-isoindole-5-sulfonamide.

19. The compound of claim 1 which is 6-chloro-2,3-dihydro-2-[3-[4-(4-fluoro-2-methoxyphenyl)-1-piprazinyl]propyl]-3-oxo-1H-isoindole-5-sulfonamide.

20. The process for treating hypertension comprising systemically administering to a mammal in need of such treatment an antihypertensive effective amount of a compound of claim 1 or a pharmaceutically acceptable salt thereof.

21. The process of claim 20 wherein the compound is 6-chloro-2,3-dihydro-2-[3-[4-(2-methoxyphenyl)-1-piperazinyl]propyl]-3-oxo-1H-isoindole-5-sulfonamide.

22. The pharmaceutical composition comprising an antihypertensive amount of a compound of claim 1 or a pharmaceutically acceptable acid addition salt thereof and a pharmaceutically acceptable carrier.

23. The composition of claim 22 wherein the compound is 6-chloro-2,3-dihydro-2-[3-[4-(2-methoxyphenyl)-1-piperazinyl]propyl]-3-oxo-1H-isoindole-5-sulfonamide.

* * * * *